(12) United States Patent
Avasarala et al.

(10) Patent No.: US 10,557,340 B2
(45) Date of Patent: Feb. 11, 2020

(54) ULTRASONIC BORESCOPE FOR DRILLED SHAFT INSPECTION

(71) Applicant: Aver Technologies, Inc., Woodbridge, VA (US)

(72) Inventors: Swamy Avasarala, Woodbridge, VA (US); Pranav Avasarala, Woodbridge, CA (US)

(73) Assignee: Aver Technologies, Inc., Woodbridge, VA (US)

( * ) Notice: Subject to any disclaimer, the term of this patent is extended or adjusted under 35 U.S.C. 154(b) by 11 days.

(21) Appl. No.: 16/059,244

(22) Filed: Aug. 9, 2018

(65) Prior Publication Data

US 2019/0120041 A1 Apr. 25, 2019

Related U.S. Application Data

(60) Provisional application No. 62/575,822, filed on Oct. 23, 2017.

(51) Int. Cl.
*E21B 47/00* (2012.01)
*G01N 21/954* (2006.01)

(52) U.S. Cl.
CPC ....... *E21B 47/0002* (2013.01); *G01N 21/954* (2013.01); *G01N 2201/0224* (2013.01); *G01N 2201/102* (2013.01)

(58) Field of Classification Search
CPC .......................... E21B 47/0002; G01N 21/954
See application file for complete search history.

(56) References Cited

U.S. PATENT DOCUMENTS

| | | | | |
|---|---|---|---|---|
| 4,079,625 A | * | 3/1978 | Mann ...................... | E02D 1/022 73/152.59 |
| 4,938,060 A | * | 7/1990 | Sizer ...................... | E21B 34/06 348/85 |
| 5,123,492 A | * | 6/1992 | Lizanec, Jr. ............ | E21B 17/00 166/242.1 |

(Continued)

FOREIGN PATENT DOCUMENTS

| DE | 202 13 658 U1 | 2/2003 |
|---|---|---|
| JP | 3120951 B2 | 10/2000 |

OTHER PUBLICATIONS

GPE, Inc., Product Bulletin, Miniature Drilled Inspection Device (Mini-sid), available at https://web.archive.org/web/20160603170031/http://www.gpe.org/products/miniSID.htm, Jun. 3, 2016, 2 pages.

*Primary Examiner* — Irfan Habib
(74) *Attorney, Agent, or Firm* — Bookoff McAndrews, PLLC

(57) ABSTRACT

A borescope includes a housing extending from a first end toward a second end, the housing including a first transparent viewing section extending circumferentially around a longitudinal axis of the housing and defining an exterior of a portion of the housing; a first imaging assembly configured to rotate about the longitudinal axis of the housing, and also pivot relative to the longitudinal axis of the housing; and a second imaging assembly disposed within the housing, the second imaging assembly being configured to rotate about the longitudinal axis of the housing, wherein the second imaging assembly is configured to visualize a field of view exterior of the housing through the first transparent viewing section.

19 Claims, 15 Drawing Sheets

(56) References Cited

U.S. PATENT DOCUMENTS

| | | | | |
|---|---|---|---|---|
| 5,255,245 A * | 10/1993 | Clot | E21B 47/011 | 181/102 |
| 5,275,038 A * | 1/1994 | Sizer | E21B 17/203 | 340/854.7 |
| 5,355,128 A * | 10/1994 | Riordan | E21B 47/0002 | 340/854.7 |
| 5,379,216 A * | 1/1995 | Head | E21B 47/102 | 702/12 |
| 5,419,188 A * | 5/1995 | Rademaker | E21B 17/203 | 367/35 |
| 5,485,745 A * | 1/1996 | Rademaker | E21B 17/203 | 73/152.39 |
| 5,550,331 A * | 8/1996 | Thompson | E21B 47/011 | 181/102 |
| 5,587,525 A * | 12/1996 | Shwe | E21B 49/008 | 73/152.52 |
| 5,652,617 A * | 7/1997 | Barbour | E21B 47/0002 | 348/85 |
| 5,663,559 A * | 9/1997 | Auzerais | E21B 47/0002 | 250/269.1 |
| 5,717,455 A * | 2/1998 | Kamewada | G02B 23/2415 | 348/85 |
| 5,754,220 A * | 5/1998 | Smalser, Sr. | G02B 23/24 | 348/84 |
| 5,771,984 A * | 6/1998 | Potter | E21B 7/14 | 175/14 |
| 5,969,241 A * | 10/1999 | Auzerais | E21B 28/00 | 73/152.16 |
| 5,996,711 A * | 12/1999 | Ohmer | E21B 7/061 | 175/61 |
| 6,041,860 A * | 3/2000 | Nazzal | E21B 23/002 | 166/250.01 |
| 6,145,247 A * | 11/2000 | McKinnis | A01H 4/001 | 137/874 |
| 6,157,893 A * | 12/2000 | Berger | E21B 49/008 | 702/12 |
| 6,164,126 A * | 12/2000 | Ciglenec | E21B 49/10 | 73/152.01 |
| 6,229,453 B1 * | 5/2001 | Gardner | H04N 7/183 | 340/853.8 |
| 6,275,645 B1 * | 8/2001 | Vereecken | G01N 33/24 | 250/254 |
| 6,281,489 B1 * | 8/2001 | Tubel | E21B 47/00 | 166/250.15 |
| 6,307,199 B1 * | 10/2001 | Edwards | G01V 5/125 | 250/269.3 |
| 7,002,620 B1 * | 2/2006 | Rutledge | E21B 47/0002 | 175/45 |
| 7,187,784 B2 * | 3/2007 | Tawfiq | E21B 47/0002 | 166/250.01 |
| 8,022,983 B2 * | 9/2011 | Clark | E21B 47/0002 | 348/85 |
| 8,151,658 B1 * | 4/2012 | Ding | E21B 47/00 | 73/865.8 |
| 8,169,477 B2 | 5/2012 | Tawfiq et al. | | |
| 2004/0160514 A1 * | 8/2004 | Tawfig | E21B 47/0002 | 348/85 |
| 2012/0026306 A1 * | 2/2012 | Mitra | G01N 29/0654 | 348/61 |
| 2012/0143004 A1 * | 6/2012 | Gupta | A61B 1/00096 | 600/117 |
| 2014/0182373 A1 * | 7/2014 | Sbihli | G01N 27/902 | 73/488 |
| 2014/0268541 A1 * | 9/2014 | Coombs | H05K 7/00 | 361/679.41 |
| 2015/0029500 A1 * | 1/2015 | Ward | G02B 23/2484 | 356/241.6 |
| 2016/0245178 A1 * | 8/2016 | Bhabhrawala | B64D 15/20 | |
| 2016/0348500 A1 * | 12/2016 | Piscsalko | G01V 9/00 | |

* cited by examiner

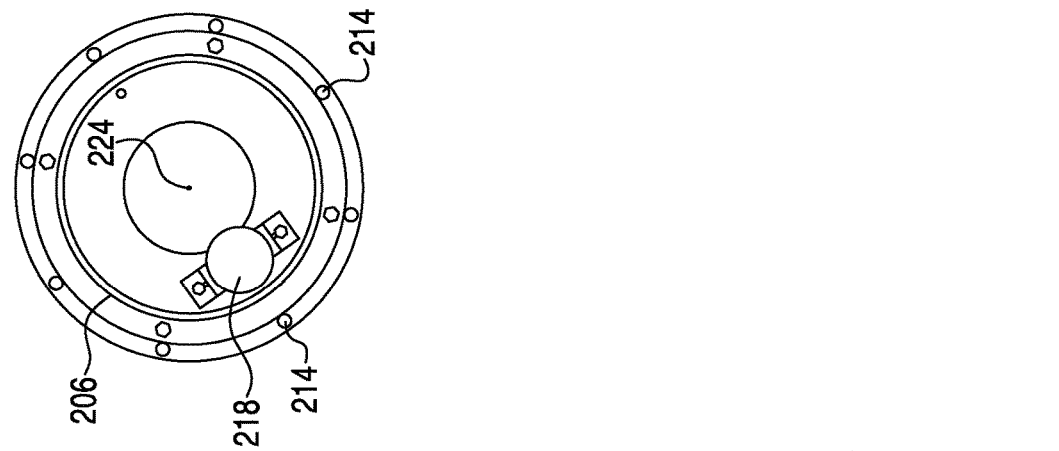
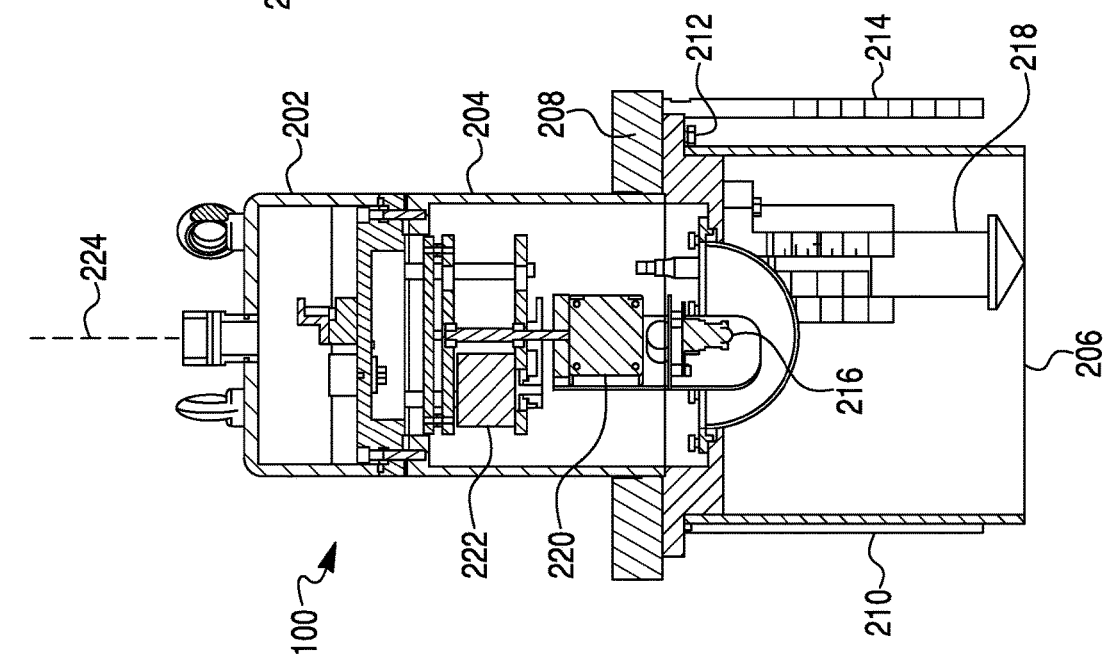
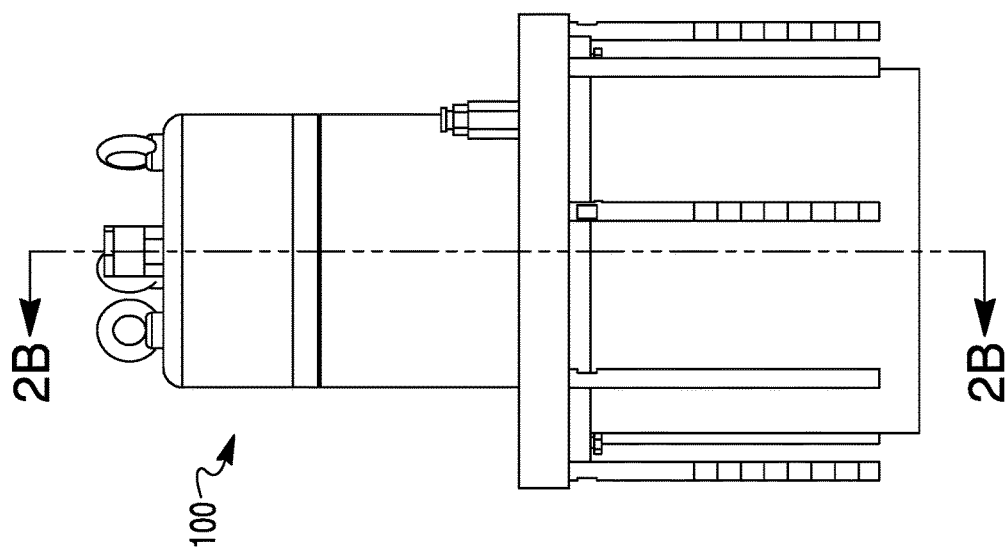

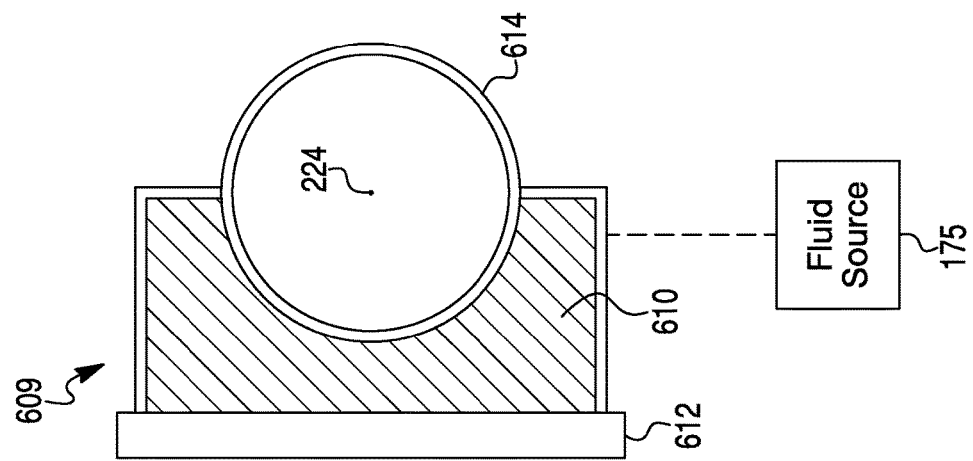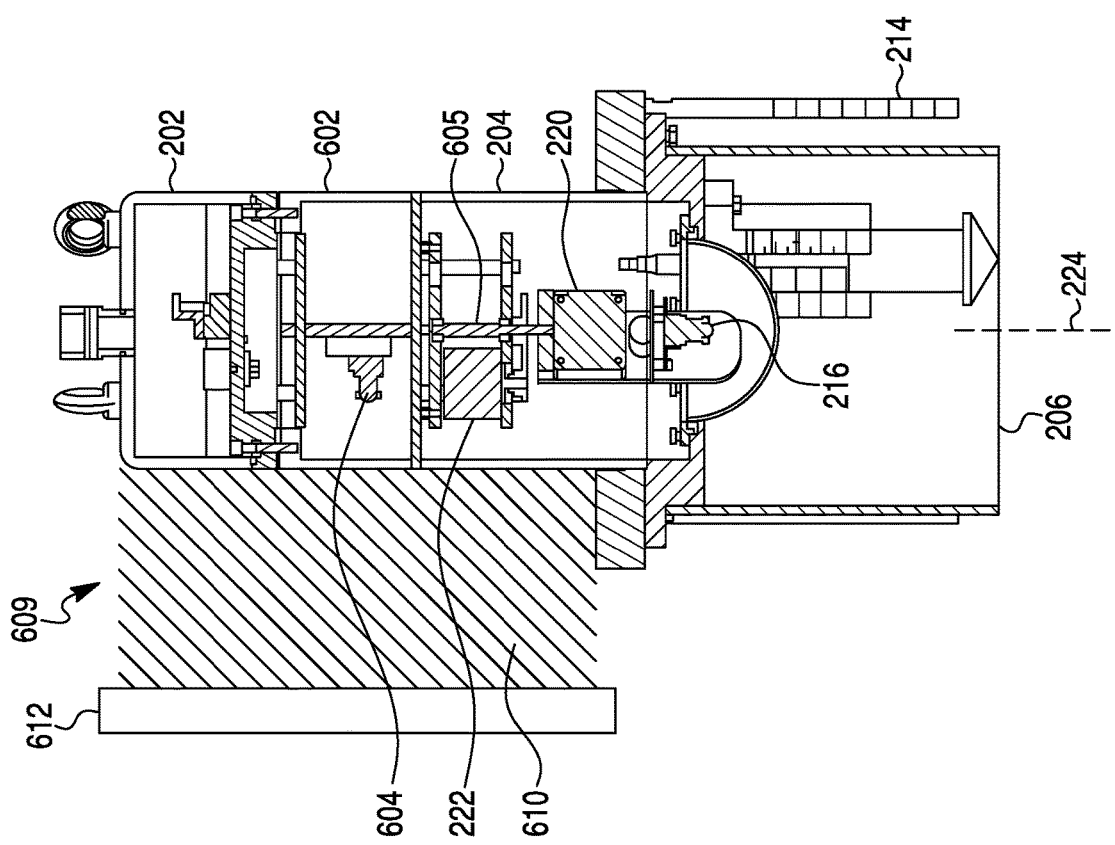

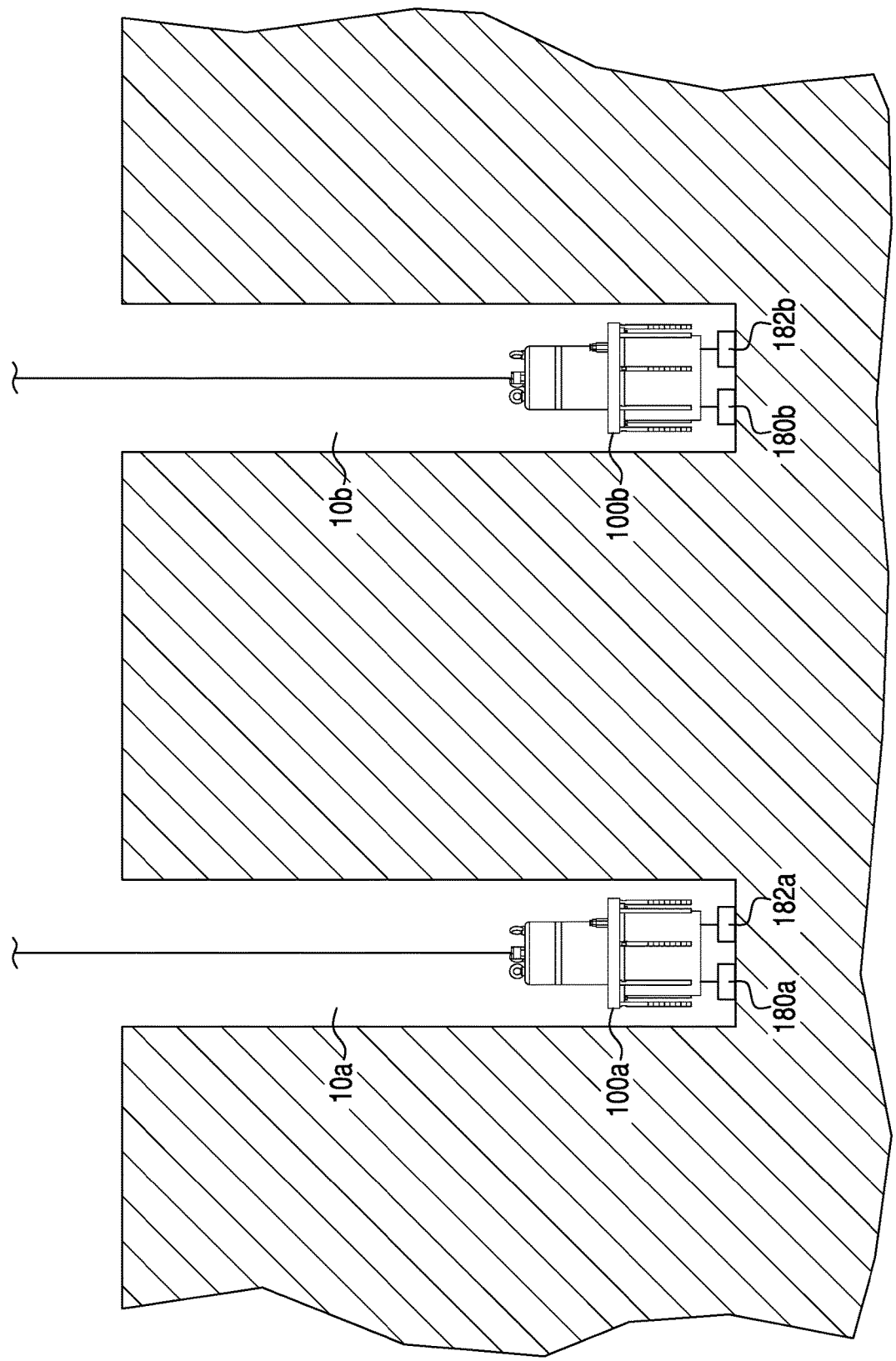

ULTRASONIC BORESCOPE FOR DRILLED SHAFT INSPECTION

CROSS-REFERENCE TO RELATED APPLICATIONS

This application claims the benefit of priority under 35 U.S.C. 119 of U.S. Provisional Patent Application No. 62/575,822, filed on Oct. 23, 2017, which is incorporated by reference herein in its entirety.

TECHNICAL FIELD

The disclosure relates generally to a borescope system for use in inspecting and profiling drilled shafts, also referred to as bores or boreholes, using multiple cameras and ultrasonic sensors. In particular, the disclosure relates to a portable system for inspecting and profiling relatively large drilled construction shafts that may improve inspection efficiency in terms of maneuverability, information gathering, data recording, data analyzing, and data qualifying.

INTRODUCTION

Drilled construction shafts that are subsequently filled with concrete or similar materials provide support for many large building and infrastructure projects. For this reason, field engineers, and inspectors involved in preparing such shafts are particularly concerned with ensuring that the load transfers in side resistance and in end bearing are consistent with any assumptions made during the design phase.

Normally, project design methods assume that drilled shafts are constructed under competent supervision with ample quality control and the finished foundation will be durable and have structural integrity. However, such assumptions are not always warranted. For example, the foundation boreholes constructed are roughly cylindrical in shape. However, the theoretical volume of bore is not same as the actual volume of the bore due to reasons such as hole size being greater than the bit used to create the hole, caving on the side of the bore, etc. Unless project specifications and procedures are closely followed in the field, for example, the final shaft may have defects that can influence its structural and bearing capacity when filled. Therefore, the inspection and profiling of the drilled shafts and the record keeping associated with the shaft construction are important and require careful attention.

Defects of a finished support structure and the conditions under which such defects occur may involve a number of causes. For example, defects typically result from one or more of the following: 1) over stressing the soil beneath the shaft base due to insufficient bearing (contact) area or because of unconsolidated materials located at the shaft base; 2) excessive mixing from mineral slurry, which can affect the development of concrete strength and/or formation of voids and cavities within the set concrete; and 3) structural discontinuities and/or deviations from the true vertical line causing local, undesirable stress concentrations. In general, these and other defects can result in insufficient load transfer reducing the bearing capacity of the final structure and/or causing excessive settling during service.

To develop the required end bearing capacity, the drilled shaft should be inspected so that undesirable debris may be removed prior to concrete placement. Shaft failures have been attributed to insufficient borehole cleaning, and cleaning the base of boreholes often require special tools. Although the operation sounds simple, a typical cleaning process involves several steps including visually inspecting the borehole, sounding the base of the shaft by a weight attached to a chain, and obtaining samples of the side walls and the base. Based on the results of the visual, sounding, and sampling inspections, a trained inspector determines whether the borehole must be cleaned or otherwise altered before concrete placement. The inspector usually bases his or her decision on the condition of the borehole and the amount of sedimentary deposits at the base. If the inspector determines that cleaning is warranted, several methods may be used, including air lifting, using a clean-out-bucket, or removing debris and unwanted material with a submerged pump.

SUMMARY

In one aspect, the disclosure is directed to a borescope that may include a housing extending from a first end toward a second end, the housing including a first transparent viewing section extending circumferentially around a longitudinal axis of the housing and defining an exterior of a portion of the housing; a first imaging assembly configured to rotate about the longitudinal axis of the housing, and also pivot relative to the longitudinal axis of the housing; and a second imaging assembly disposed within the housing, the second imaging assembly being configured to rotate about the longitudinal axis of the housing, wherein the second imaging assembly is configured to visualize a field of view exterior of the housing through the first transparent viewing section.

A shaft may extend at least partially through the housing, wherein the first imaging assembly and the second imaging assembly are both configured to rotate simultaneously about the longitudinal axis of the housing by rotation of the shaft. The borescope may include a transparent observation chamber having a first end disposed at or adjacent to the second end of the housing, and extending away from both the first end and the second end of the housing, toward a second end. The second end of the housing may be configured to transition between a closed configuration where an exterior of the observation chamber forms a fluid-tight seal around a volume, and an open configuration where fluid can move into and out of the observation chamber through the second end. The borescope may include one or more rods at or adjacent to the second end of the housing, wherein: each of the one or more rods extends from the second end of the housing and away from both the first end and the second end of the housing; and each of the one or more rods includes a plurality of graduated markings forming a scale indicative of length, wherein each scale is visible to the first imaging assembly through the transparent observation chamber. The borescope may include an expandable sleeve coupled to an exterior of the housing, wherein the expandable sleeve is configured to move from a collapsed position to an expanded position via application of a fluid through the sleeve. The borescope may include a rigid support at a radially outermost portion of the expandable sleeve, the rigid support enclosing an opening through which the fluid can exit the expandable sleeve, wherein the second imaging assembly is configured to visualize a field of view exterior of the housing through the opening and the expandable sleeve. The expandable sleeve may be coupled to the exterior of the housing by a transparent frame disposed circumferentially around the housing. In the expanded position, the expandable sleeve may extend only partially around a circumference of the housing. The borescope may include an ultrasonic sensor at or adjacent to the second end of the housing, wherein the ultrasonic sensor is configured to determine a thickness of sediment disposed at a bottom of a borehole. The borescope may include a first ultrasound sensor configured to generate ultrasound waves; and a reflector movable toward and away from the first ultrasound sensor along the longitudinal axis, or along a first axis parallel to the longitudinal axis, wherein the reflector is configured to reflect the ultrasound waves generated by the first ultrasound back toward the first ultrasound sensor, and the first ultrasound sensor is configured to determine a time-of-flight for a wave to travel from the first ultrasound sensor to the reflector, and then back to the first ultrasound sensor. The reflector may be movable between a fully compressed position and a fully extended position. The reflector may be disposed closer to the first ultrasound sensor when in the fully compressed position than when in the fully extended position. The borescope may include a biasing member configured to bias the reflector toward the fully extended position. The borescope may include a rod having a first end and a second end, wherein the reflector is disposed at the first end of the rod; and a tapered block disposed at the second end of the rod, wherein the tapered block tapers radially inward in a direction away from both the first end and the second end of the housing. The borescope may include a second ultrasound sensor configured to rotate about the longitudinal axis of the housing; and a controller configured to receive measurements from the second ultrasound sensor to determine a volume of a borehole in which the borescope is located. The borescope may include a depth sensor configured to determine a depth of the borescope, wherein the controller is configured to receive measurements from the depth sensor, wherein determination of the volume of the borehole also is based on the measurements from the depth sensor.

In another aspect, the disclosure is directed to a borescope that may include a housing extending from a first end toward a second end; a first imaging assembly coupled to the housing; a first ultrasound sensor configured to generate ultrasound waves; and a reflector movable toward and away from the first ultrasound sensor along a longitudinal axis, wherein the reflector is configured to reflect the ultrasound waves generated by the first ultrasound back toward the first ultrasound sensor, and the first ultrasound sensor is configured to determine a time-of-flight for a wave to travel from the first ultrasound sensor to the reflector, and then back to the first ultrasound sensor.

The reflector may be movable between a fully compressed position and a fully extended position. The reflector may be disposed closer to the first ultrasound sensor when in the fully compressed position than when in the fully extended position. The borescope may include a biasing member configured to bias the reflector toward the fully extended position. The borescope may include a rod having a first end and a second end, wherein the reflector is disposed at the first end of the rod; and a tapered block disposed at the second end of the rod, wherein the tapered block tapers radially inward in a direction away from both the first end and the second end of the housing.

In yet another aspect, the disclosure is directed to a borescope that may include a housing having extending from a first end toward a second end; a first imaging assembly coupled to the housing; an ultrasound sensor configured to rotate about a longitudinal axis of the housing; and a controller configured to receive measurements from the ultrasound sensor to determine a volume of a borehole in which the borescope is located.

The borescope may include a depth sensor configured to determine a depth of the borescope, wherein the controller is configured to receive measurements from the depth sensor, wherein determination of the volume of the borehole also is based on the measurements from the depth sensor.

BRIEF DESCRIPTION OF THE DRAWINGS

FIG. 2A is a side view of a measurement assembly of the system of FIG.

FIG. 2B is a cross-sectional view of the measurement assembly of FIG. 2A, taken along line 2B-2B.

FIG. 2C is an end bottom view of the measurement assembly of FIG. 2A.

FIG. 6A is a cross-sectional view of a dual camera assembly according to another embodiment of the disclosure.

FIG. 6B is an end view of a portion of the assembly of FIG. 6A.

FIG. 11 is an illustration of multiple measuring assemblies deployed in separate boreholes.

DETAILED DESCRIPTION

Embodiments of the disclosure provide, among other things, a system for accurately inspecting and profiling relatively large construction boreholes such as those prepared for building and various infrastructure drilled shaft foundations. The disclosure may help provide an accurate visual inspection and volume profile of boreholes to construct deep foundations or slurry walls. Embodiments of the disclosure may determine the strength and thickness of the materials at the bottom of a borehole, a volume of a borehole, the quality of rock surrounding a borehole, as well as the physical and electrical properties, such as, the pressure and the temperature of the slurry in the borehole. This may be accomplished by a portable system utilizing at least one camera and ultrasonic sensors in a watertight assembly. The system of the present disclosure provides a device for full drilled shaft inspection that a single user can operate.

In one embodiment, an inspection system of the disclosure collects data in analog and/or digital form and is capable of providing digital information to a computing device using a cable. In yet another embodiment, the camera and ultrasonic sensors are controlled wirelessly from a computing device. Thus, it is economical and convenient in terms of the number of required personnel and efficient in storing and retrieving the needed information.

The present disclosure may be particularly well-suited for inspection in waterways projects and may provide clear vision in environments where visibility is limited. Moreover, the features of the present disclosure described herein may be less laborious and easier to implement than currently available techniques, as well as being economically feasible and commercially practical.

Figure 1:
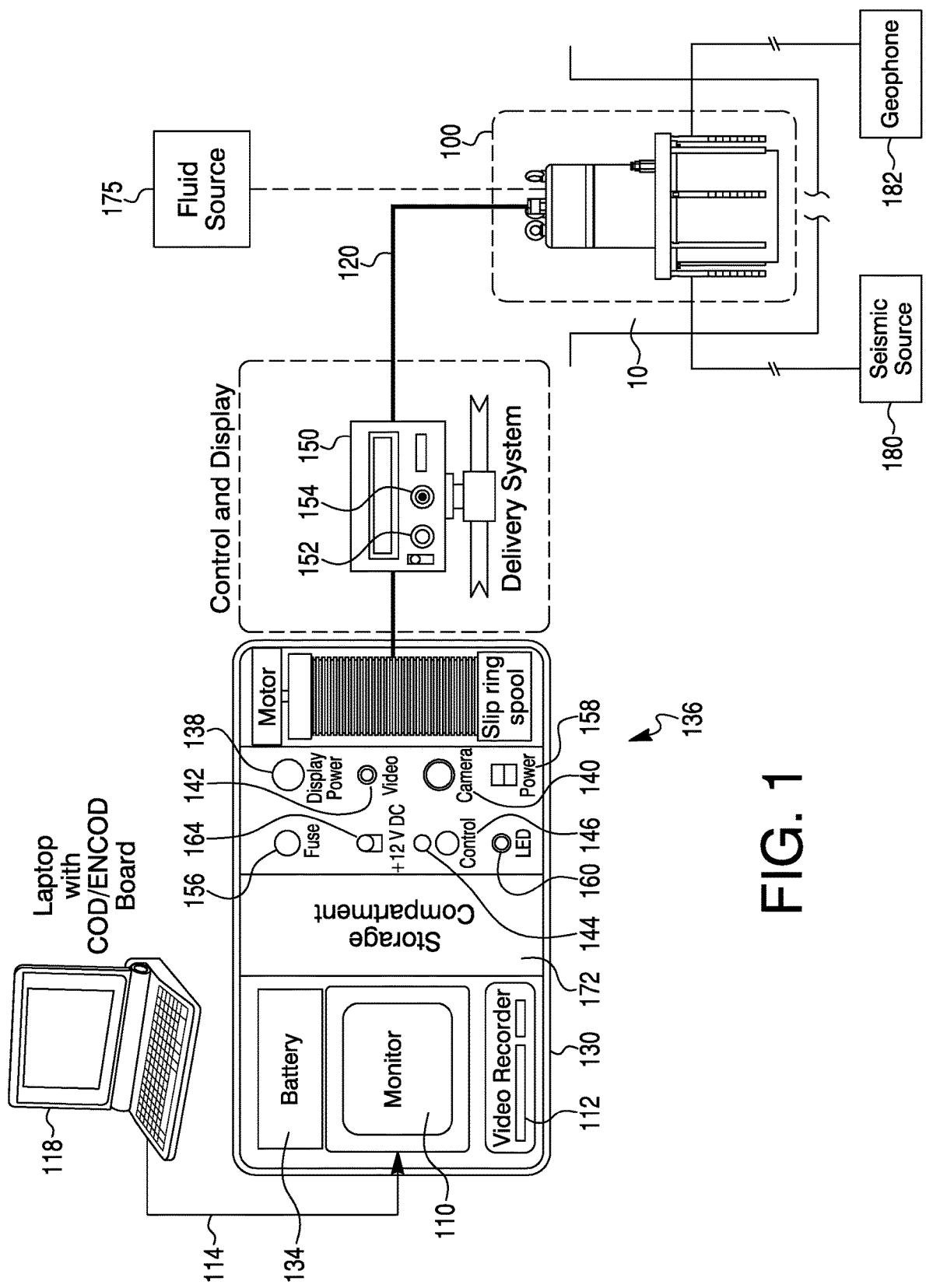
FIG. 1 is a schematic diagram of a borescope system for visually inspecting and profiling drilled shafts according to an embodiment of the disclosure.

Referring now to the drawings, FIG. 1 illustrates a borescope system in block diagram form. As shown, the system includes a measurement assembly 100 connected to a display 110 (e.g., a relatively small, portable video display or television) for visually inspecting a borehole. A typical borehole is several feet in diameter (e.g., about nine feet) and has an even greater depth (e.g., about 150 feet). It is to be understood, however, that a borehole describes any opening in the ground that has either a generally cylindrical geometry of a few inches to several feet in diameter and depth or a generally rectangular cutoff wall in the ground with a few inches to several feet in width/depth. Drillers may sink a borehole using a drilling rig or a hand-operated rig. The machinery and techniques to advance a borehole vary considerably according to manufacturer, geological conditions, and the intended purpose. The borehole can be dry or wet (at least partially filled with transparent, translucent, or opaque fluid). The borehole can be self supported, cased, or a pipe pile. The ratio of the size of the borehole to the measurement assembly 100 can be about 1:1 (so long as the housing fits within the borehole), about 2:1, about 3:1, about 4:1, about 5:1, about 10:1, or about 28:1.

As described in detail below, the present system may be used to visually inspect boreholes to construct deep foundations or slurry walls using at least one camera. In addition, the system may be able to determine the strength and characteristics of the materials at the bottom of the boreholes, the volume of the borehole; and the physical and electrical properties, the pressure, and the temperature of the slurry in the borehole.

According to embodiments of the disclosure, measurement assembly 100 generates images and measurements of the interior surfaces of the borehole while suspended in the borehole. In one embodiment, the borescope system provides a line 114 to a computer 118 for displaying and recording the captured images and measurements. In the embodiment shown, measurement assembly 100 communicates with the computer 118 via a power-control cable 120 (also referred to as an umbilical cord). Measurement assembly 100 communicates with computer 118 according to, for example, an RS232 standard, although any other suitable mechanism also is contemplated. It is to be understood that computer 118 may be used in addition to or instead of the display 110 and video recorder 112 for recording the video images of the interior of the borehole and measurements of soil characteristics generated by measurement assembly 100.

The borescope system of the disclosure also includes a case 130 for housing, storing, and transporting various components of the system. The case 130 houses a rechargeable, or otherwise replaceable, battery 134 for supplying power to the various components of the system. In some embodiments, duplicate power and battery systems may be incorporated. An appropriately wired connector panel 136 may provide electrical connections between the various components such as the battery 134, measurement assembly 100, display 110, and/or computer 118.

Although computer 118 is shown as a laptop computer in FIG. 1, other computer configurations are easily adapted for use with the present disclosure, including, for example, tablets (e.g., construction- or military-grade tablets), smart phones, and the like. Moreover, computer 118 may be self-powered (e.g., independently battery powered), receive power from battery 134, or receive power from an external source independent of the borescope system.

In the illustrated embodiment, battery 134 supplies power to display 110 and recorder 112 via a display power connection 138 and a power line (not shown). Battery 134 also supplies power to measurement assembly 100 via a camera input 140, an ultrasonic sensor input 144 and the power-control cable 120. In the embodiment shown in FIG. 1, the line 114 supplies camera data and sensor measurements to computer 118 (or another external monitor) via a video connector 142. The connector panel 136 also includes a control input 146 described below.

As will be explained in greater detail below, a controller 150 controls measurement assembly 100. The controller 150 is connected on one side, by an umbilical cord containing power-control cable 120 to computer 118. Controller 150 is connected on another side to control input 146 on connector panel 136 via a cable or wireless communication. As shown in FIG. 1, controller 150 further includes a pan controller 152 and a tilt controller 154. Control signals generated by controllers 152, 154 are transmitted to measurement assembly 100 via power-control cable 120. Additionally, the RS232 link between computer 118 and measurement assembly 100 is established via controller 150. Thus, it is possible to generate and transmit computer controlled input information to measurement assembly 100 via controller 150. Likewise, computer 118 can receive information pertaining to at least one camera or ultrasonic sensor from measurement assembly 100 via controller 150.

The connector panel 136 also provides access to a power supply fuse 156, as well as a system power switch 158 and a power indicator 160. Although it is anticipated that the borescope system will often operate using the battery 134, the system also may be connected directly to an external power source using a power line (not shown) connected via a power connector 164. The external power line and power connector 164 also may be used to recharge the battery 134 when the system is not being used. Although the embodiment shown in FIG. 1 contemplates the use of a 12 volt power system, the borescope system of the present disclosure is in no way limited to 12 volt systems. Additionally, the case 130 also includes at least one storage compartment 172 for storing various components of the borescope system when the system is not in use or being transported. A borescope system according to the disclosure may permit control, measurement, and/or display of the depth of ultrasonic penetrometer and camera assembly depth, and/or descending velocity as well as electrical conductivity, pressure, thickness, and/or temperature of the slurry contained in the borehole.

Measuring assembly 100 also may include a seismic source 180 and a geophone (or other suitable sensor) 182. Seismic source 180 may be any device that generates controlled seismic energy used to perform both reflection and refraction seismic surveys. Seismic source 108 may provide single pulses or continuous sweeps of energy, generating seismic waves, which travel through the ground. In one example, seismic source 180 may be a hammer (e.g., a pneumatic hammer), which may strike a metal plate to generate the seismic waves. Some of the seismic waves generated by seismic source 180 may reflect and refract, and may be recorded by geophone 180.

Seismic source 180 and geophone 182 may be used to investigate shallow subsoil structure, for engineering site characterization, or to study deeper structures, or to map subsurface faults. The returning signals from the subsurface structures may be detected by geophone 182 in known locations relative to the position of the subsurface structures.

As shown in FIG. 11, multiple measuring assemblies (e.g., assemblies 100a and 100b) disposed in separate boreholes (e.g., 10a and 10b) can be equipped with a seismic source and geophone to provide additional information regarding subsurface structures in a given area. For example, a seismic source 180a may be activated to create seismic waves detectable by both a geophone 182a on the same measuring assembly, as well as being detectable by a geophone 182b from a different measuring assembly located in a different borehole. Similarly, seismic source 182b may be activated to create seismic waves detectable by both geophone 182b and geophone 182a.

Referring now to FIGS. 2A and 2B, measurement assembly 100 includes a camera 216 and an ultrasonic penetrometer 218. As described above, the size of the borehole may be much larger than the size of the measurement assembly 100 (e.g., about 28 times or more). In one embodiment, the width of measurement assembly 100, including camera 216, is substantially less than the diameter of the borehole under inspection (e.g., approximately ten inches compared to several feet). The center of the measurement assembly 100 may include a central axis 224. Camera 216 and ultrasonic penetrometer 218 are positioned concentrically about central axis 224.

Camera 216 may be housed within an assembly 204. Assembly 204 is generally cylindrical in this embodiment and constructed using a rigid material such as aluminum. It is to be understood, however, that other materials, such as polyvinyl chloride (PVC), may be suitable for protecting camera 216. Observation chamber 206 provides camera 216 with viewing access to, e.g. a borehole, while protecting camera 216 from damage due to contact with the surfaces being inspected. Any suitable transparent material, including, e.g., glass or transparent plastic could be used to construct observation chamber 206.

Supporting or protective rods 214 are attached to assembly 204 and surround observation chamber 206. Supporting rods 214 protect chamber 206 when the system is lowered into a borehole. Supporting rods 214 may be circumferentially spaced apart from one another about axis 224, and may include graduated markings (indicative of length, e.g., a ruler) along their respective lengths. When measurement assembly 100 is positioned at the bottom of a borehole, measurement assembly 100, including supporting rods 214, may sink into a soft material at the bottom of the borehole. When viewed by a camera 216, the markings of supporting rods 214 may help determine how far measurement assembly 100 has sunk into the bottom of the borehole.

Observation chamber 206 is a generally cylindrical structure constructed of rigid, transparent plastic or a similar material, although other suitable shapes are also contemplated. Observation chamber 206 may have a larger diameter than assembly 204. In an alternative embodiment, observation chamber 206 is made of a flexible, durable, transparent plastic. Observation chamber 206 is particularly well-suited for use in slurry-filled boreholes.

Boreholes are often filled with a viscous mud, or slurry, especially in waterways projects. The slurry, however, obscures the view of the side walls and bottom of the filled borehole. Observation chamber 206 provides camera 216 with a viewing interface. In operation, a system operator lowers camera 216 into observation chamber 206. According to the disclosure, a fluid source 175 may supply pressurized air and/or water (e.g., a gas and a liquid simultaneously) to the observation chamber 206 to push out slurry and mud from the space enclosed by observation chamber 206 to provide clear view of the borehole bottom or side surface even though measurement assembly 100 is submerged in the slurry. Observation chamber 206 thus helps define a viewing area for camera 216 in situations where a camera could not otherwise view the walls or bottom of the borehole. By moving the viewpoint of camera 216 in observation chamber 206, the operator may obtain images and videos of the borehole's interior surface. A light source (LED) may be located on the side of observation chamber 206 e.g., on mounting brackets for camera 216, to illuminate the viewing area while camera 216 is capturing images and videos of the interior surface of the borehole. In some embodiments, observation chamber 206 may have a closed bottom end. In such an embodiment, measuring assembly 100 may be lowered into a borehole while flush with the inner circumferential surface of the borehole, to enable a user to view the inner circumferential surface. The closed bottom end may be achieved via a removable end cover to enable measuring assembly 100 to have multiple operating modes, e.g., one mode with an open bottom end where fluid can move into and out of observation chamber 206, and another mode with a closed bottom end where an exterior of observation chamber 206 forms a fluid tight seal around an interior volume of observation chamber 206.

Measuring assembly 100 also includes ultrasonic penetrometer 218 for sensing physical characteristics of the soil and bore. Ultrasonic penetrometer 218 may be used to measure characteristics of soil such as sediment thickness, calibrated resistance, and slurry density. The present disclosure may be used to determine the structural adequacy of a borehole by capturing clear and accurate images (and videos) of the borehole's bottom and side surfaces. Cleanliness of the bottom and sides of the borehole from any soil or rock residues is an important factor for determining whether the borehole is adequate for constructing deep foundations or slurry walls. Also, evaluating borehole adequacy may include identifying cracking in pipe piles or defects in borehole casing.

FIG. 2C depicts the bottom view of measurement assembly 100 showing ultrasonic penetrometer 218 surrounded by the observation chamber 206 and supporting rods 214. Ultrasonic penetrometer 218 may be displaced adjacent to the periphery of observation chamber 206 accordingly (shown in FIG. 2C), so the penetrometer 218 does not interfere with the movement or view area of camera 216. In such an embodiment, ultrasonic penetrometer 218 may be offset from axis 224 and camera 216.

Referring back to FIG. 2B, a top cover assembly 202 connects to assembly 204 on one side (shown in FIG. 2B) and to the control and display system on the other side via power-control cable 120 (as shown in FIG. 1). Assembly 204, top cover assembly 202, observation chamber 206, and supporting rods 214 are assembled to create a substantially watertight protective housing for the electronics of measurement assembly 100.

Figure 3:
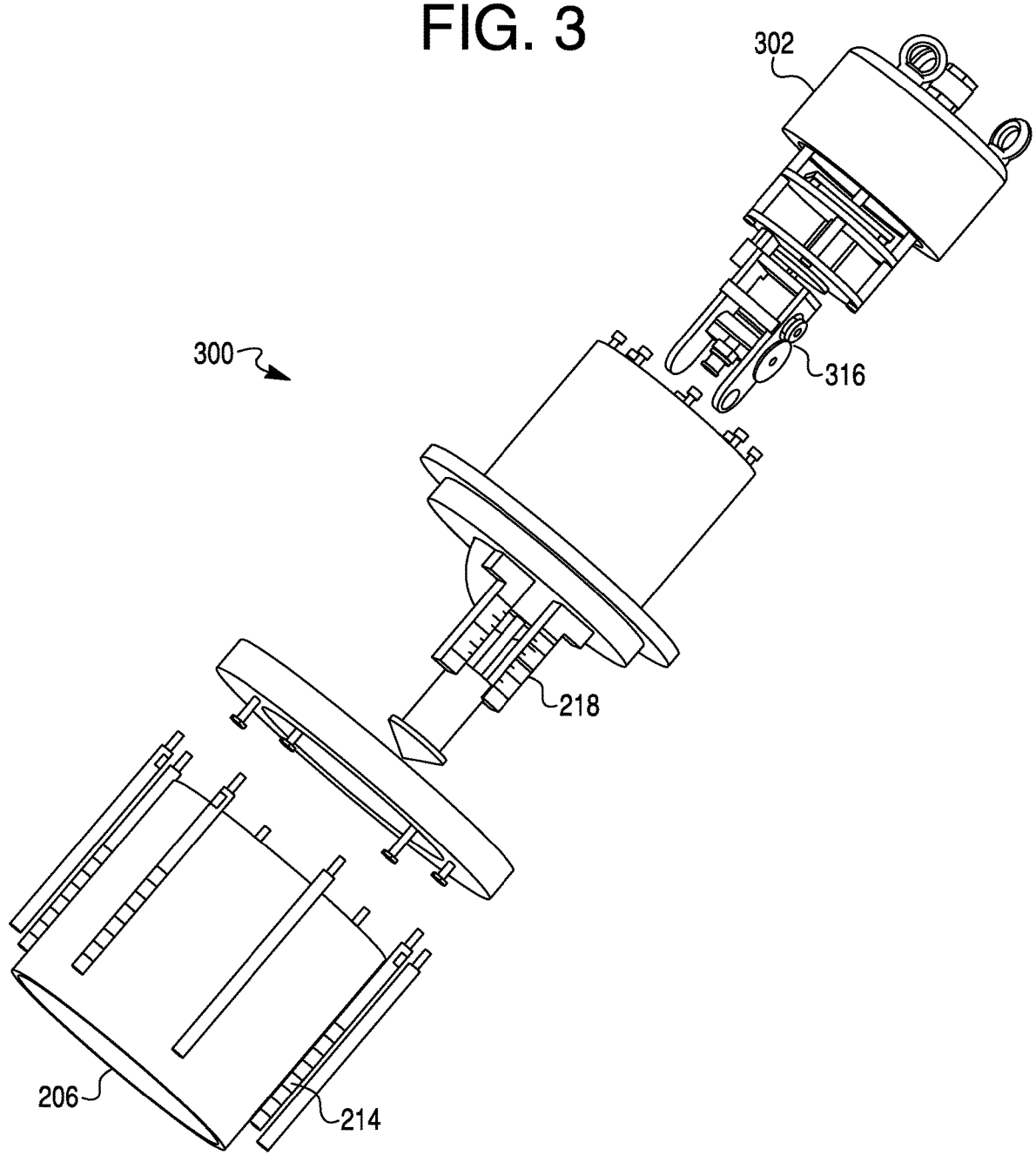
FIG. 3 is an exploded view of an ultrasonic penetrometer assembly and camera assembly.

FIG. 3 depicts an exploded side view of measurement assembly 100. In particular, FIG. 3 depicts an ultrasonic penetrometer 218 coupled to assembly 204, chamber 206, supporting rods 214, and camera assembly 316. The supporting rods 214 surround glass chamber 206 for protection of ultrasonic penetrometer 218 and camera assembly 316.

Figure 4A:
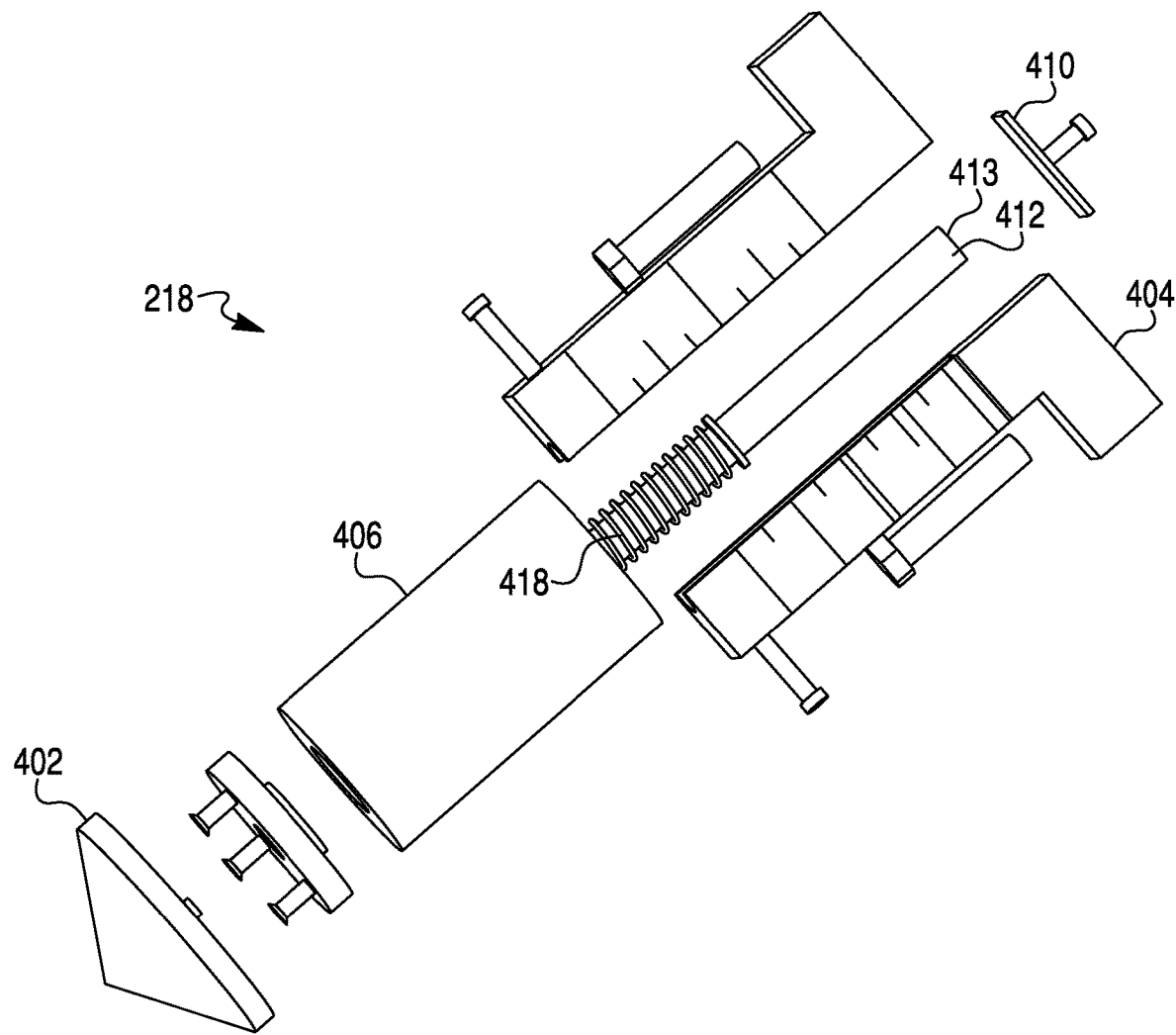
FIGS. 4A and 4B are exploded side views of the ultrasonic penetrometer assembly of FIG. 3.
Figure 4B:
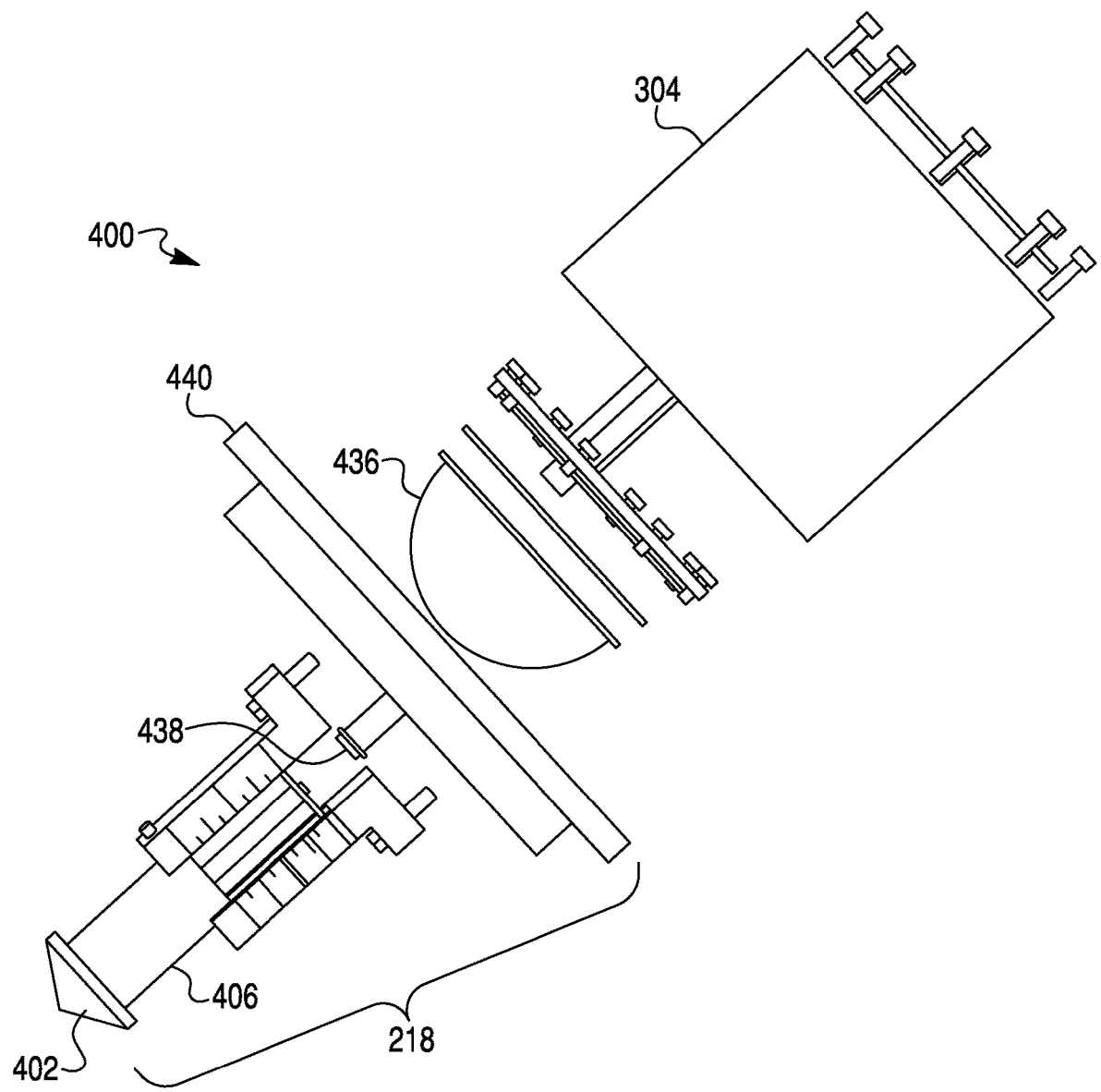

FIGS. 4A and 4B show ultrasonic penetrometer 218 including an ultrasonic sensor 438, a measurement scale 404, and a cone shaped protrusion (tapered block) 402. Protrusion 402 may be tapered radially inward when extending in a direction toward the bottom of the borehole (and otherwise away from assembly 600). Ultrasonic sensor 438 is mounted to the front plate 440. Ultrasonic sensor 438 can be used for in-air and non-contact object detection that detect objects within a defined area.

The ultrasonic penetrometer 218 measures the stiffness and sediment thickness of the bottom surface of the borehole using, for example, a cone shaped protrusion 402, a sensor block 406 coupled to a spring (biasing member) 418 on a sensor rod 412, and a measurement scale 404. The ultrasonic penetrometer 218 measures the exact displacement or absolute position of moving sensor rod 412 connected to spring 418, which is representation of the strength of materials at the bottom of the borehole.

The ultrasonic sensor 438 may generate an analog signal proportional to the distance from ultrasonic sensor or transducer 438 to the sensor rod 412. Ultrasonic sensor 438 uses high frequency waves to detect and localize sensor rod 412, and measure the time of flight for a wave that has been transmitted to and reflected back from proximal end 413 of sensor rod 412. Proximal end 413 thus may be a reflector configured to reflect ultrasound waves back toward ultrasonic sensor 438. The time of flight is the time necessary for the ultrasonic wave to travel to the proximal end 413 of sensor rod 412 from ultrasonic sensor 438, and the back to ultrasonic sensor 438. The measured time of flight may be shorter or longer as the distance to the sensor rod 412 changes according to the compression of spring 418. For example, when spring 418 is fully compressed (e.g., by a completely rigid borehole bottom), the ultrasound wave emitted from ultrasonic sensor 438 may have a relatively short time of flight, as compared to when the borehole bottom is soft, and spring 418 is fully extended. In the fully compressed position, proximal end 413 may be disposed closer to ultrasonic sensor 438 than when in the fully extended position. Spring 418 may be biased toward the fully extended position.

In the above illustrated embodiment, the time-of-flight measurements help determine sediment thickness of the soil at the bottom of the borehole. The compression of spring 418 reflects the hardness of the soil at the bottom surface of the borehole experienced by sensor block 402. For example, the harder the soil at the bottom surface of the borehole, the more compression that is observed by spring 418. However, if the soil at the bottom surface of the borehole is relatively soft, less compression is observed by spring 418. Therefore, the calculated time of flight is relatively low for harder soil compared to softer soil. The measurements obtained are accurate because the movement of the proximal end 413 of sensor rod 412 corresponds exactly to the penetration of 402 into the bottom of the borehole.

Ultrasonic sensor 438 has better accuracy to make measurements independent of material, color, transparency, and texture than other tools used for direct measurements, such as, e.g., infrared sensors for a metal obstacle. Other methods of direct measurements have their own associated problems. For example, an LVDT linear position sensor may be immune to magnetic fields, and its output may vary depending on vibration, altitude, and temperature. A very precise, accurate, and stable voltage source is required in such a system, which makes a system using LVDT very costly.

Additionally, measurement scale 404 displays the proportional positions of the compressed spring 418 and sensor rod 412 from their original positions. The position markings on measurement scale 404 may be captured by the camera assembly 216. The obtained position measurements may be used to visually confirm the measurements obtained by ultrasonic sensor 438.

In one embodiment, the ultrasonic penetrometer 218 is capable of determining sediment thickness at the bottom of a borehole based on, e.g., the depth in which rods 214 penetrate the surface.

Figure 5:
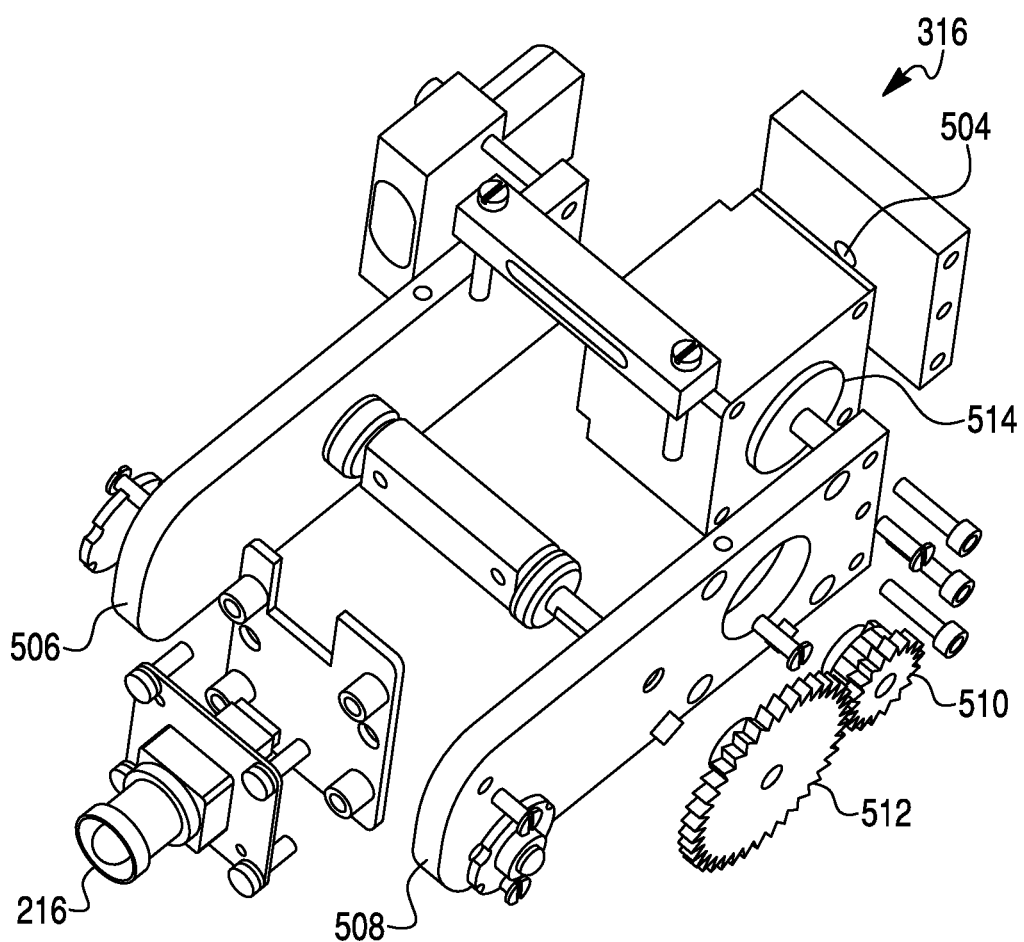
FIG. 5 is a schematic view of the camera assembly of FIG. 3.

FIG. 5 is a schematic view of camera assembly 316 of the borescope system according to the present disclosure. Camera assembly 316 includes a miniature color or black and white charge coupled (CCD) camera 216 with a wide angle (e.g. approximately 180 degrees) lens. In one embodiment, the width of camera assembly 316, including the miniature camera 216, is substantially less than the diameter of the borehole under inspection (e.g., a few inches compared to several feet). Camera 216 is protected by side plates 504, 506, and 508. These side plates 504, 506, and 508 are constructed using a rigid material such as, e.g., aluminum. It is to be understood, however, that other materials, such as PVC, may be suitable for use in the side plates. For example, one embodiment of the present disclosure uses an aluminum side plates enclosed in a PVC casing.

The camera assembly 316 also encloses a tilt and pan gear mechanism including gears 510 and 512. A system operator controls the tilt and pan gear mechanism to rotate camera 216 through a wide range of motion (e.g., 360 degrees in-plane and 180 degrees out-of-plane). Electronic control board 514 controls the tilt and pan gear mechanism and camera 216 in response to operator inputs from controller 150 via power unit 132 and power-control cable 120 (see also FIG. 1). Electronic control board 514 may provide instructions to vertical servo motor 220 (as shown in FIG. 2B) for tilting camera 216 and horizontal servo motor 222 (also shown in FIG. 2B) for rotating it. Electronic control board 514 provides servo motors 220 and 222 with electrical control signals in response to operator inputs from the tilt and pan controllers 152, 154 of controller 150 (see FIG. 1). In particular, control board 514 includes a micro-controller with an analog-to-digital (A/D) converter and a pulse width modulation output driver. The micro-controller receives analog input signals from tilt and pan controllers 152, 154 and converts the received signals to pulse width modulated output signals for accurately controlling the position of servo motors 220 and 222 using control and driver techniques that are known in the art.

The functionality of the tilt and pan gear mechanism may be further described by reference to the vertical servo motor 220 and the horizontal servo motor 222. The tilt mechanism and vertical servo motor 220 constitute a first rotational motion stage for rotating camera 216 in a plane defined by vertical axis 224 relative to the observation chamber 206, i.e., tilting camera 216 up to approximately 180 degrees (±90 degrees), as camera 216 is suspended in the borehole. Likewise, the pan mechanism and horizontal servo motor 222 constitute a second rotational motion stage for rotating camera 216 about vertical axis 224 over approximately 360 degrees as camera 216 is suspended in the borehole. By manipulating tilt and pan gear mechanism, also referred to as a motion control mechanism, the operator can control and direct a camera viewing angle or line of sight, which in turn enables the operator specify areas of the borehole for viewing and inspection.

Referring back to FIG. 4B, an abrasion resistant transparent dome 436 provides camera 216 with viewing access while protecting the camera 216 from possible damage due to contact with the surfaces being inspected. Although the transparent dome 436 in the embodiment illustrated in FIG. 4B is constructed of plastic, any number of transparent materials could be used with the borescope system of the present disclosure. The camera 216 is further configured by the operator to zoom and focus automatically while taking images. The camera is also controlled by the system operator for zooming in/out and manipulating focus wirelessly in real-time.

In an alternative embodiment, FIG. 6A depicts a camera assembly 600 having two cameras (216 and 604). The second camera 604 may be substantially similar to camera 216 set forth above with respect to FIGS. 2B and 2C. In some examples, cameras 216 and 604 may be used in combination to capture images and videos of the bottom of the borehole and the sides of the borehole. For example, camera 216 may be used to capture images of the bottom and sides of the borehole, or of only the bottom of the borehole. In the example where camera 216 is configured to capture images of only the bottom of the borehole (and not the sides of the borehole), In other examples, the first camera 216 may still be controlled by the servo motors (220 and 222 described with respect to FIG. 2B). Motor 222, which is used to rotate camera 216 about axis 224 by rotating shaft 605, also may control the rotation of camera 604 about axis 224, providing both cameras 216 and 604 with 360 degree viewing capability. Thus, the rotation of shaft 605 may simultaneously rotate both cameras 216 and 604. It is also contemplated that a separate motor (not shown) may rotate camera 604 about axis 224.

Assembly 204 may be substantially similar in this embodiment as described above with respect to FIG. 2B, except that in a dual-camera arrangement, assembly 204 may be lengthened to include a transparent viewing section 602 through which second camera 604 may view the sides of a borehole. Thus, second camera 604 may visualize a field of view exterior to assembly 600 through viewing section 602. Viewing section 602 may circumferentially enclose a volume within assembly 204 where second camera 604 and stepper motor 602 are located. Viewing section 602 may include substantially transparent materials, including, e.g., tempered glass or a transparent polymer.

Figure 6C:
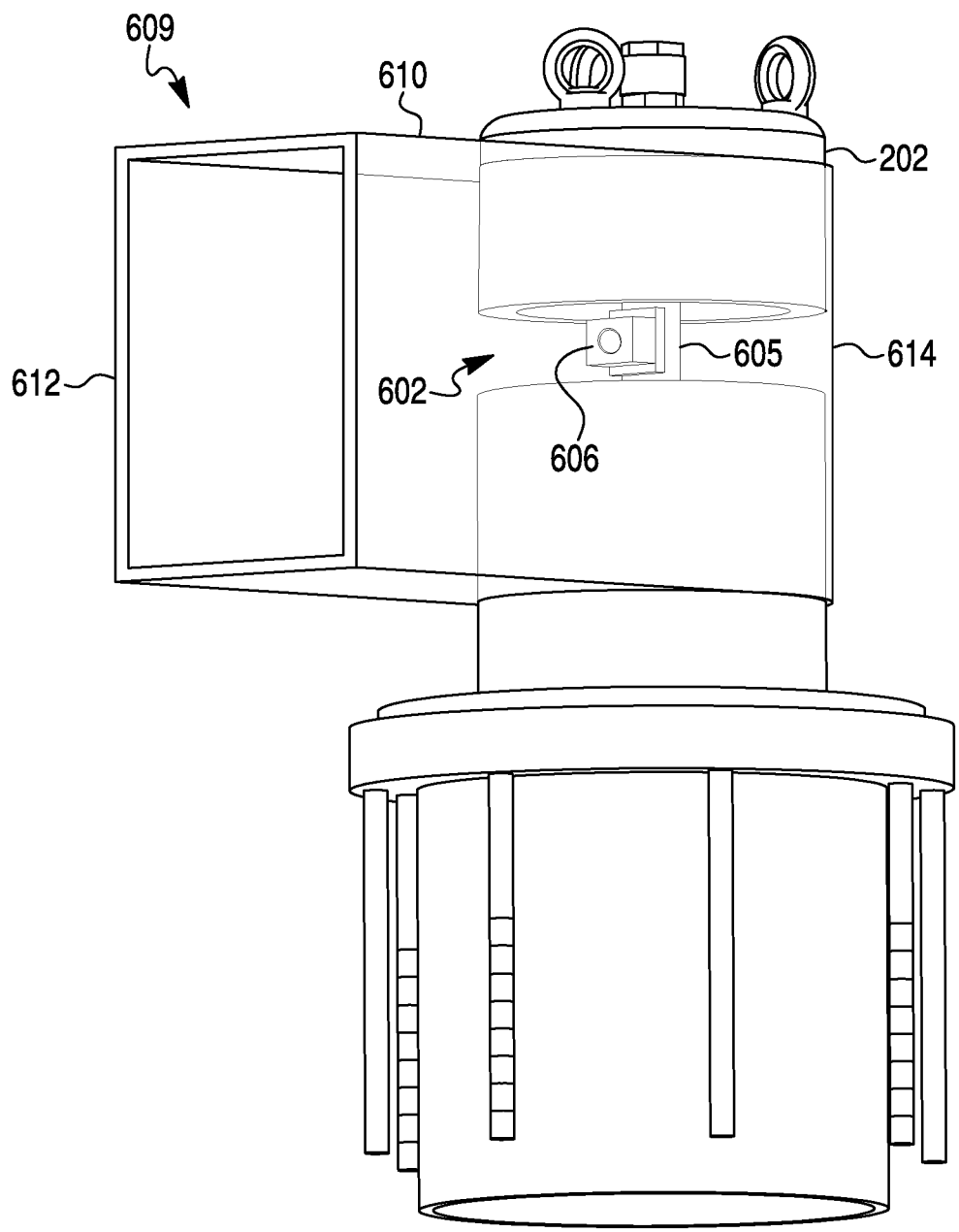
FIG. 6C is a perspective view of the assembly of FIG. 6A.
Figure 6D:
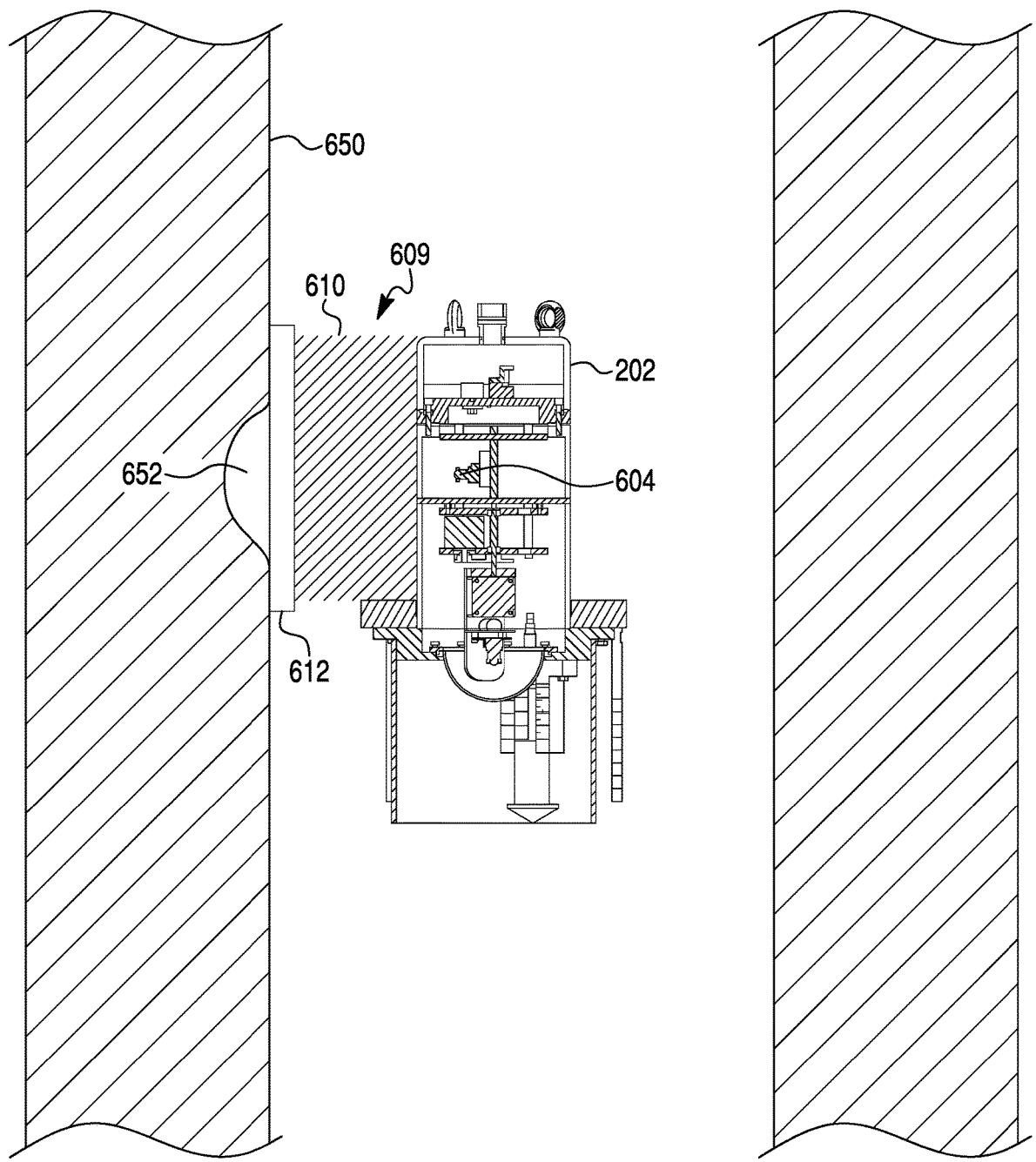
FIG. 6D is an illustration of the assembly of FIG. 6A deployed in a borehole.

Additionally, an expandable member 609 may be coupled to an outer circumferential surface of the dual camera assembly 600 by a transparent frame 614 (shown in FIGS. 6B and 6C) to help provide second camera 604 with clear view of the sides of a bore. Frame 614 may include a sleeve that slides over the housing of assembly 600 and may be secured to the housing while expandable member 609 is aligned over at least a portion of viewing section 602. Expandable member 609 may be an inflatable or otherwise expandable transparent member including an expandable sleeve 610 and a support 612. Support 612 may be disposed at a radially outermost portion of sleeve 610, and includes an opening 614. Expandable member 609 may be inflated by air, water, or another suitable material delivered via a source at ground level through a suitable line or conduit (e.g., fluid source 175). Expandable member 609 may be inflated or expanded before or after assembly 600 is lowered into a borehole. In use, an operator may position assembly 600 so that support 612 and opening 614 is adjacent to and/or in contact with a side surface 650 of a borehole (as shown in FIG. 6D). Support 612 and other outer surfaces of expandable member 609 may include a reinforcing material, e.g., a clear plastic, to help prevent puncture of expandable member 609 during contact with the side surface of the borehole. Support 612 may be positioned around a depression 652 in the side surface 650 of the borehole, forming a partial seal around depression 652. The fluid from fluid source 175 that inflates expandable member 609 also may flush fluid and debris from depression 652 to enable viewing of depression 652 by camera 604. In other words, second camera 604 may visualize a field of view exterior to assembly 600 through opening 614, support 612, and sleeve 610. In some examples, expandable member 609 may extend around only a portion of the circumference of assembly 204 (as shown in FIG. 6B), while in other examples, expandable member 609 may extend around an entirety of the circumference of assembly 204. When expandable member 609 extends around only a perimeter of assembly 204, expandable member 609 may be fixed relative to assembly 204, or may be rotatable around assembly 204. When expandable member 609 is fixed relative to assembly 204, an entirety of assembly 600 may be rotated to enable a 360 degree view of the borehole. However, when expandable member 609 is rotatable relative to assembly 204, the entirety of assembly 600 need not be configured to rotate within the borehole. Rotation of expandable member 609 relative to assembly 204 may be achieved via, e.g., one or more motors, rails, tracks, and the like.

Figure 7B:
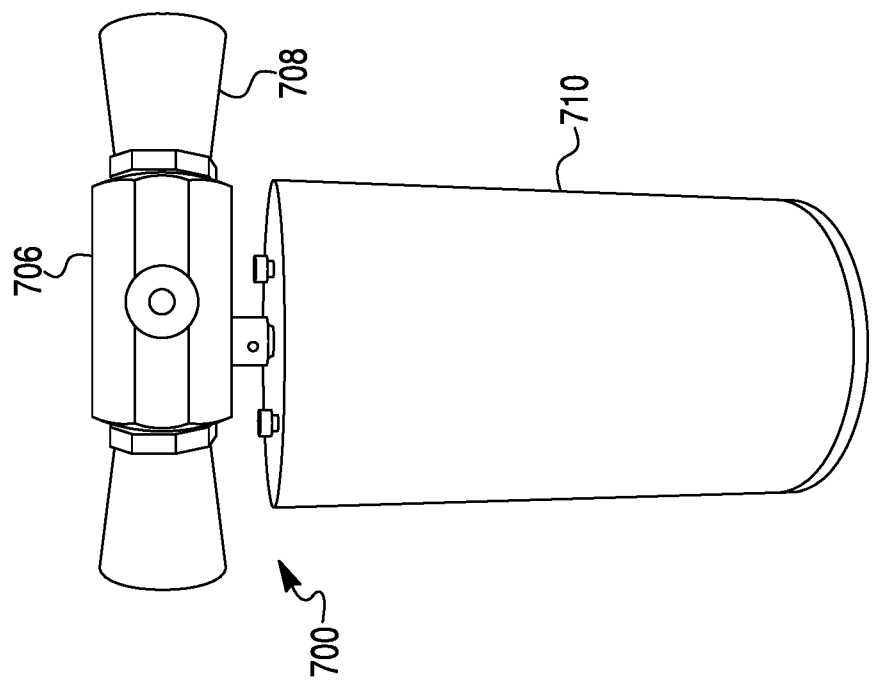
FIG. 7B is a side view of the profiling assembly of FIG. 7A.
Figure 7A:
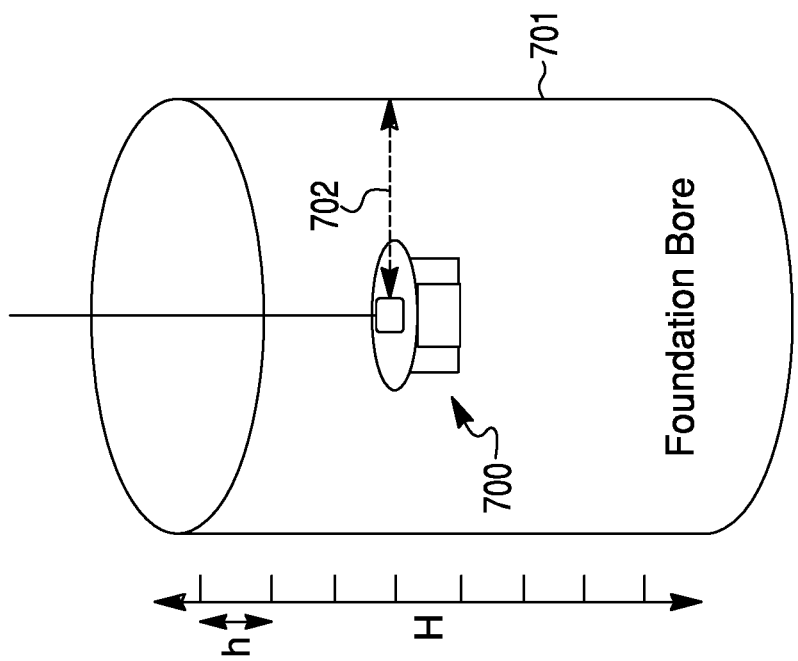
FIG. 7A is a schematic view of a profiling assembly inside a foundation bore.

FIGS. 7A and 7B depict a profiling assembly 700 for profiling a borehole. Typically, a foundation bore 701 is roughly in a cylindrical shape. Measuring the actual volume of the bore may not be possible when the bore is filled with slurry and mud.

In general, there are three commonly used types of sensors (ultrasonic, infrared, and laser) for single ended non-contact distance measurement. These sensors measure distance according to a transmitting energy and deducing parameters based on the reflected energy from an obstacle. In a borehole, the distance to the inner wall may need to be measured at various levels along the length of the bore. The medium between the device and the bore wall can be either air or bentonite slurry/water. The laser-based distance measurement sensor may not be used because the bentonite slurry is usually opaque (which may interfere with the path of the laser). Infrared waves may not be suitable for long-range underwater measurement as they may be heavily absorbed in water. Furthermore, the diameter of the bore may vary between 1 m and 3 m. Most of the infrared sensors available have a range of about 120 cm, whereas the bore diameter can be as high as 3 m.

In contrast, ultrasonic sensors may have the ability to travel through opaque media, including, e.g., bentonite slurry and water. Also, ultrasonic sensors have been effectively used for SONAR and can measure higher distances. Thus, an ultrasonic sensor 706 may be used in profiling assembly 700 to help determine a profile of a borehole.

The profiling assembly 700 may compute a volume of bore 701 and provide a 3D-profile of the bore using a non-contact technique. An actuating mechanism 710 allows the sensor to profile the entire circumference of the bore in situations where the characteristics (e.g., density, temperature, viscosity etc.) of the medium vary to a great extent. Actuating mechanism 710 may include controllers, motors, and the like, which may help rotate ultrasonic sensor 706, enabling ultrasonic sensor 706 to survey an entire circumference of a respective borehole. To measure the actual volume of a bore, the volume of the bore is split into a set of segments, and the radius of each segment is measured to calculate the respective segment volume. The data received from profiling assembly 700 is used to develop a three dimensional model of the bore to help the operator visualize the borehole on a display.

In the above-illustrated embodiment, a microcontroller is used for controlling motor that operates the ultrasonic sensor 706. To find a radius 702, the distance between the center of bore and wall of bore is needed. Ultrasonic sensor 706 generates an analog signal proportional to the distance between the center and side of the bore. An analog input pin in the microcontroller receives the analog signal from ultrasonic sensor 706 and gives the distance between sensor and side of bore in centimeters or another suitable dimension. To measure the radius of various segments, the ultrasonic sensor 706 needs to be rotated at each level across the entire bore, for which a stepper motor is used, which in turn controlled by the microcontroller. A digital pulse with a specific pattern is generated using the microcontroller, and sent as output to control the stepper motor. Ultrasonic sensor 706 is mounted on the stepper motor shaft, and may be controlled to make distance measurements in each step of motor for one complete rotation.

In addition, a depth sensor (e.g., a depth wheel provision) provides the height of each level where measurements are taken. This process is repeated at different depths of the bore across its total height, to determine an approximate total volume of bore. The sensor assembly 700 is lowered into the bore at fixed intervals of height (h) (e.g., at various levels across bore), as determined by the operator by means of a depth sensor. Based on the intervals, and the overall depth (H), the bore will be divided into n vertical steps/levels. At each step/level, the radial profile will be measured by ultrasonic sensor 706. The approximate volume of the bore is computed according to the combined knowledge of radial profile and the depth (H). It is further contemplated that one or more portions of profiling assembly 700 may be coupled to assembly 100 or assembly 600. For example, sensor 706 may be disposed on a rotatable shaft that extends exterior to cover assembly 202. Alternatively, sensor 706 may be disposed on shaft 605. In this alternative embodiment, the outer housing may include an open circumferential portion to enable sensor 706 to direct ultrasound waves to the sides of the borehole.

Profiling assembly 700 may be used even when the medium within the borehole changes with depth. Non-contact measurement techniques have an inherent dependency on the medium in which they operate. Ultrasound travels through different mediums at different velocity due to number of factors such as density, temperature, etc. Also, the attenuation of ultrasound varies in each medium. Typically, the medium of the bore varies across the height of the bore (e.g., the bore may be completely empty or may be filled with fluid at various depths). When the device moves from one medium to another, (e.g., air to slurry), the medium change may be sensed by observing distance values. For example, the speed of sound in water is about five times the speed of sound in air. There may be a substantial variation in the distance measured from the sensor 706 when there is a change in medium. Accordingly, this information is used to identify the change in medium.

In order to negate the effect of the medium change, ultrasonic sensor 706 may need to be calibrated for each medium in order to obtain reliable distance measurements. The below-explained calibration technique may eliminate the need for calibrating the sensor for different mediums, and identifies the true distance without the need to know the actual medium. This calibration technique is primarily based on analysis and rectification of error based on known factors. For example, two measurements are taken for an object by positioning a sensor away from the object at two different locations but separated by a known offset between them.

Let D cm be the actual distance from A to B. Let M1 be the first distance measurement taken from point A to B. Let M2 be another measurement, taken from point A' to B, while A' is situated at an offset distance of L cm from A.

From the above statements we know that, $$(M1 - M2) \; K = L; \text{ and } K = \frac{L}{M1 - M2};$$

To find the true distance D, we use the equation:

$$D = M1 * K.$$

By identifying the K, it is possible to approximate the actual distance value. In a yet another embodiment, M1 and M2 measurements can also be simultaneously taken, by positioning two ultrasonic sensors separated by known offset L cm. This will minimize time taken for measurement. The profiling assembly 700 may include two ultrasonic sensors in order to perform the above-explained calibration, and to minimize the time taken for measurement. It may be necessary for the ultrasonic sensor 706 to be free from obstacles while measuring and rotating. Additionally, it may be important to keep profiling assembly 700 waterproof, while allowing the ultrasonic sensor 706 to rotate freely. The experimental validation may be performed by completely submerging the sensor in water or other medium like slurry as well.

Figure 7C:
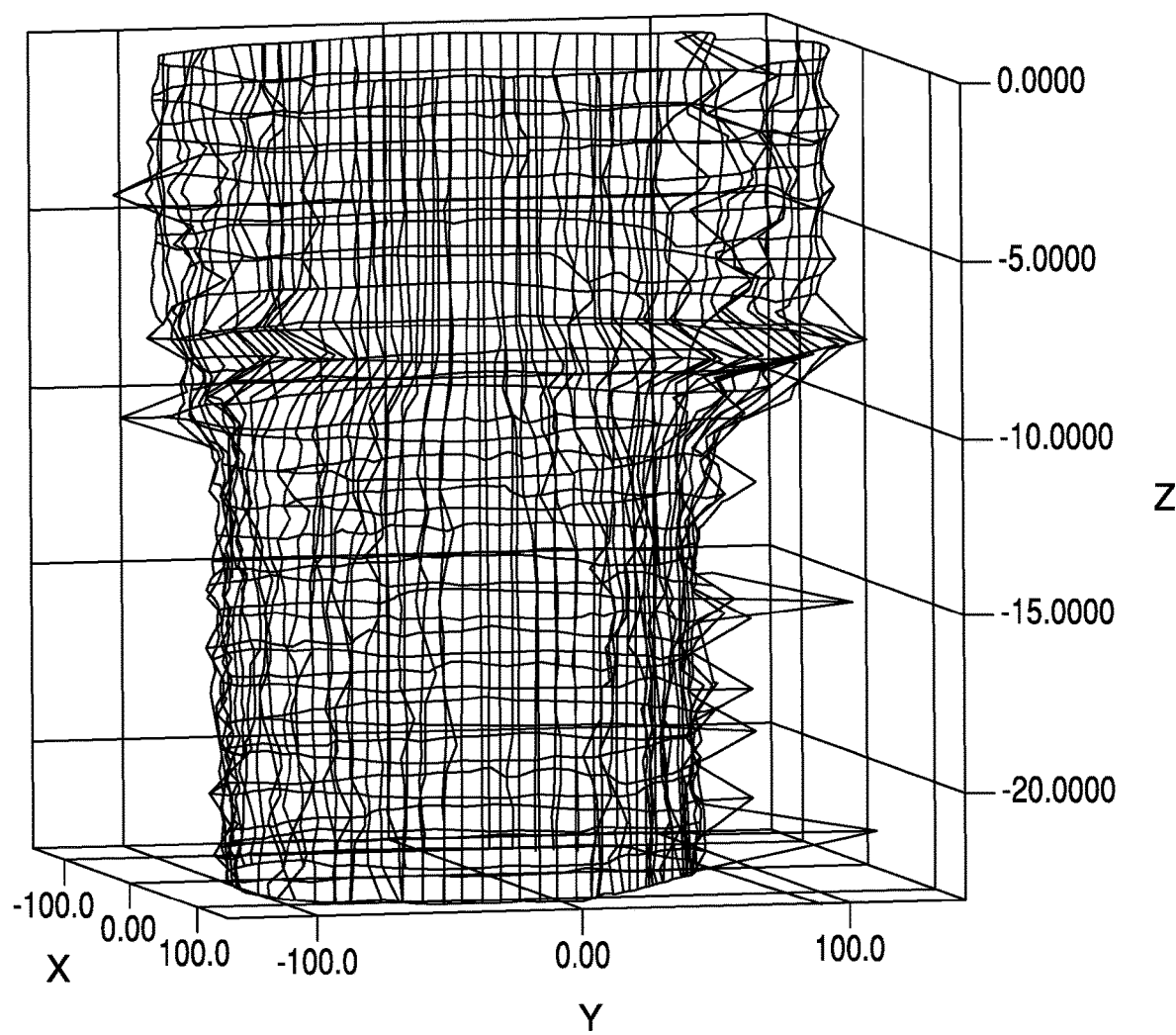
FIG. 7C is an example output developed for the assembly of FIG. 7A.

FIG. 7C depicts a 3D visualization of a borehole. The 3D plot may be automatically generated as the ultrasonic sensor 706 measures circumference of the borehole at different depths.

The system operator may select a 3D plot option on a profiling user interface (UI) to view the 3D plot of borehole. The 3D plot can be expanded for a better viewing experience.

EXAMPLE

Experiments were conducted to demonstrate the technique for underwater distance measurement. The experiments involved the measurement of circumference of an inflatable swimming pool filled with water, of controlled circumference. An inflatable swimming pool with a diameter of 3 m and height of 2 feet was filled with water and a number of experiments were performed. The prototype was submerged inside the inflatable pool. After a few minutes in water, it was operated (the sensors were rotated). No leaks were identified, indicating satisfactory underwater operation and performance.

In another experiment, the prototype was placed at the center of the pool. The diameter of the empty swimming pool was measured first. The device was made to measure the circumference of the top edge of the pool which was above water level. Since the medium of propagation was air, no calibration was required and the radial profile was obtained directly. While a few random values were obtained in the measured data, they appeared to be due to misalignment of the sensor and the edge of the pool. Readings taken were compared with actual distance (measured with tape) and were satisfactory.

In another experiment, the prototype was once again completely immersed inside the pool. The prototype was placed at the center of the pool and was made to measure the distance of a fixed point, i.e., the sensors were not rotated. Many readings were taken by altering the position of the prototype inside the pool. The actual distance (measured with tape) was compared to the reading given by the sensor. The actual distance and the sensor reading correlated with each other and changed linearly.

In yet another experiment, the prototype was completely submerged inside water and a profile of the pool was taken. The device was placed at the center of the pool and the sensors were rotated to sweep the entire pool. The variation in depth was simulated by changing the circumferential profile of the inflatable pool after each scan. Subsequently, a large number of readings were taken. The true distance was also measured at a random location using measuring tape and was compared to the calibrated sensor results.

Calibration Process

Measured radii from the primary and secondary sensors were compared to calibrate the prototype. For example, at one data point, r1 (the radius of the primary sensor) was 34, and r2 (the radius measured by the secondary sensor) was 31. The known offset between the sensors at that data point was 12. The correlation factor was governed by the equation of the known offset, divided by the difference between r1 and r2, which in the example above is equal to 4. Then, the calculated distance is equal to the correlation factor multiplied by r1, or (4*34=136 cm). The true distance measured was 162 cm. The above variation in calculated distance and true distance was due to the variation of minimum resolution exhibited by sensor due to difference in medium.

For example, a measurement of 1 cm difference between two locations will be shown as 1 cm in an air medium, giving a resolution of 1 cm, whereas a 5 cm difference between two locations will be shown only as 1 cm in water.

In another example, if r1 is 33.5 and r2 is 31, then the correlation factor is 4.8 (or 12/2.5). In this example, the calculated distance is 160.8 cm, which is approximately equal to the true distance value of 162 cm.

In some examples, sound may travel about 4.2 to 4.8 times faster in water than it does in air. As a result, the distance measured in water may be roughly 1/4.5 times the actual distance. However, if the density, temperature, etc., of the water varies, the above ratio also will vary. That said, by using the calibration technique, it will be possible to make measurements without any considerations to the change in medium.

Furthermore, many ultrasonic sensors have a finite dead zone. The dead zone of an ultrasonic sensor is the minimum range below which the sensor is unable to measure distance. Ultrasonic sensors also have a maximum range above which they cannot measure. The resolution of most ultrasonic sensors is defined in air. The resolution of the sensor also changes with changes in medium. Thus, the effective resolution of an ultrasonic sensor varies drastically when in water. The sensor used for this prototype (MB7070) had a dead zone of 20 cm, maximum range of 700 cm, and a resolution of 1 cm. All the above values are specified for air. When measuring under water, the dead zone increases to about 100 cm, and the maximum range to about 3500 cm. However, the resolution of the sensor also deteriorates to about 5 cm. As a result, any distance variations within 5 cm, inside water, may not be detected.

Also, while performing the calibration routine, the better the resolution of the sensor, the more accurate the results will be.

Figure 8:
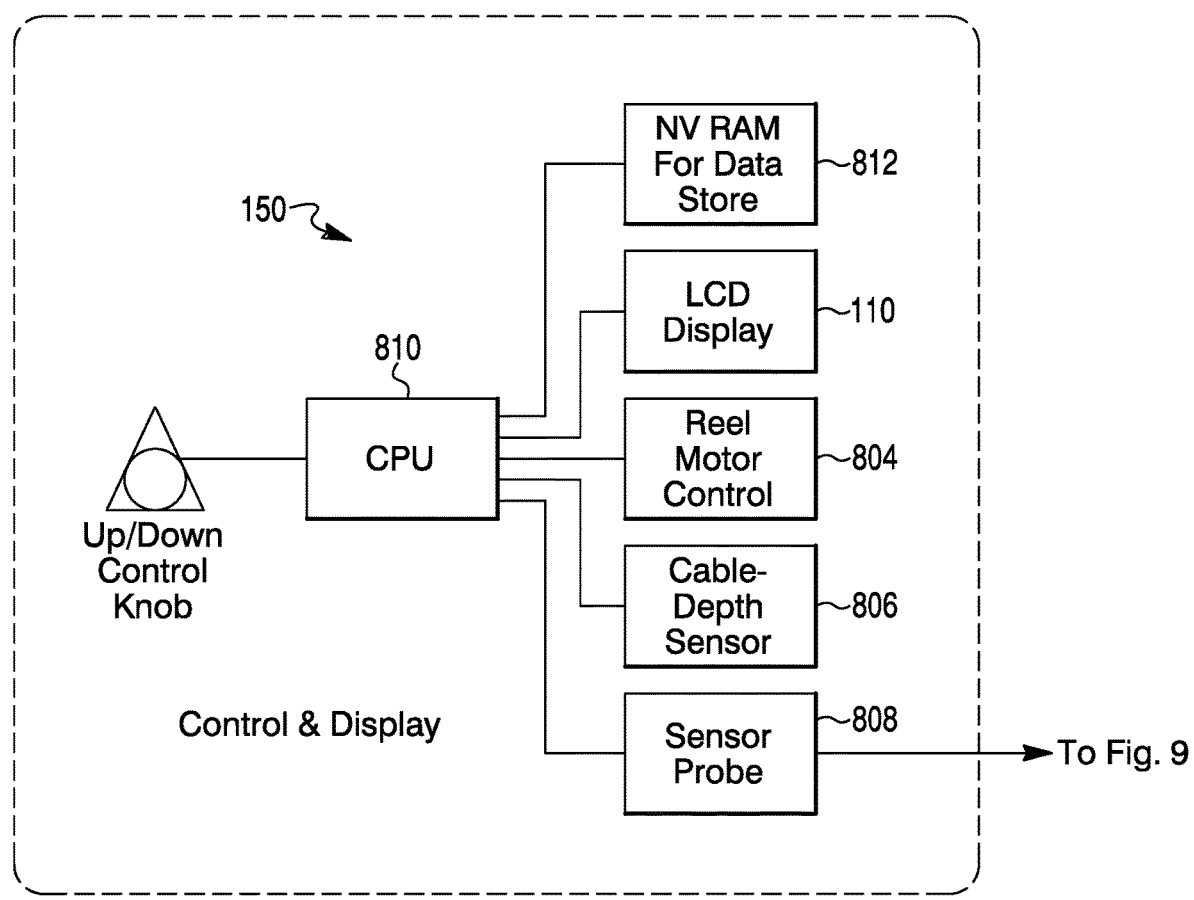
FIG. 8 is a block diagram of a borescope system for visually inspecting and profiling drilled shafts according to another embodiment of the disclosure.

FIG. 8 illustrates further aspects of the overall borescope system according to the disclosure in which computer 118 cooperates with controller 150 and display 110. In operation, a reel motor control 804 is responsive to user input via controller 150 for raising or lowering camera assembly 100 within a borehole under inspection. A cable depth sensor 806 provides information regarding the depth of measurement assembly 100 at any given instant as it drops into the drilled shaft. In addition, one or more sensor probes 808 (see FIG. 9) may provide information to central processing unit 810 regarding any of a number of characteristics of the borehole. A memory 812 associated with computer 118 stores the gathered information in this embodiment of the disclosure. In an example embodiment, the measurement assembly 100 comprises of wireless or Bluetooth transmitter. The measurements from the camera and ultrasound sensor are transmitted wirelessly to the controller 150 or a computing device (e.g. laptop, tablet) with a Bluetooth or wireless receiver.

In other words, FIG. 8 shows the components of a control and display unit according to embodiments of the disclosure. For example, sensor probes 808 encompass sensors and measurements shown in FIG. 9, including load cell 902 (for unit weight and viscosity measurements); thermocouple 904 (for temperature measurement); conductivity probe 906 (for electric conductivity measurement of the slurry); pressure gauge 908 (for slurry pressure measurement) and the ultrasonic sensor 910 (for thickness of the soil) and ultrasonic sensor 912 (for profiling the borehole). As shown, the control circuitry of FIG. 9 conditions the sensor signals and prepares them for processing by computer 118. For example, the analog sensor signals are conditioned and then multiplexed by an analog multiplexer 912 before being converted to digital signals by an analog/digital converter 914 for processing by computer 118.

Those skilled in the art are familiar with thermocouples and pressure gauges suitable for use with the disclosure. The pressure gauge 908 measures pressure on measurement assembly 100 as exerted by the slurry in the borehole and the thermocouple 904 measures temperature of the slurry. The load cell arrangement, including load cell 902, along with the reel motor control 804 and the cable depth sensor 806 are used to measure the unit weight, the viscosity of the slurry, and the depth at which the measurements are taken.

Figure 9:
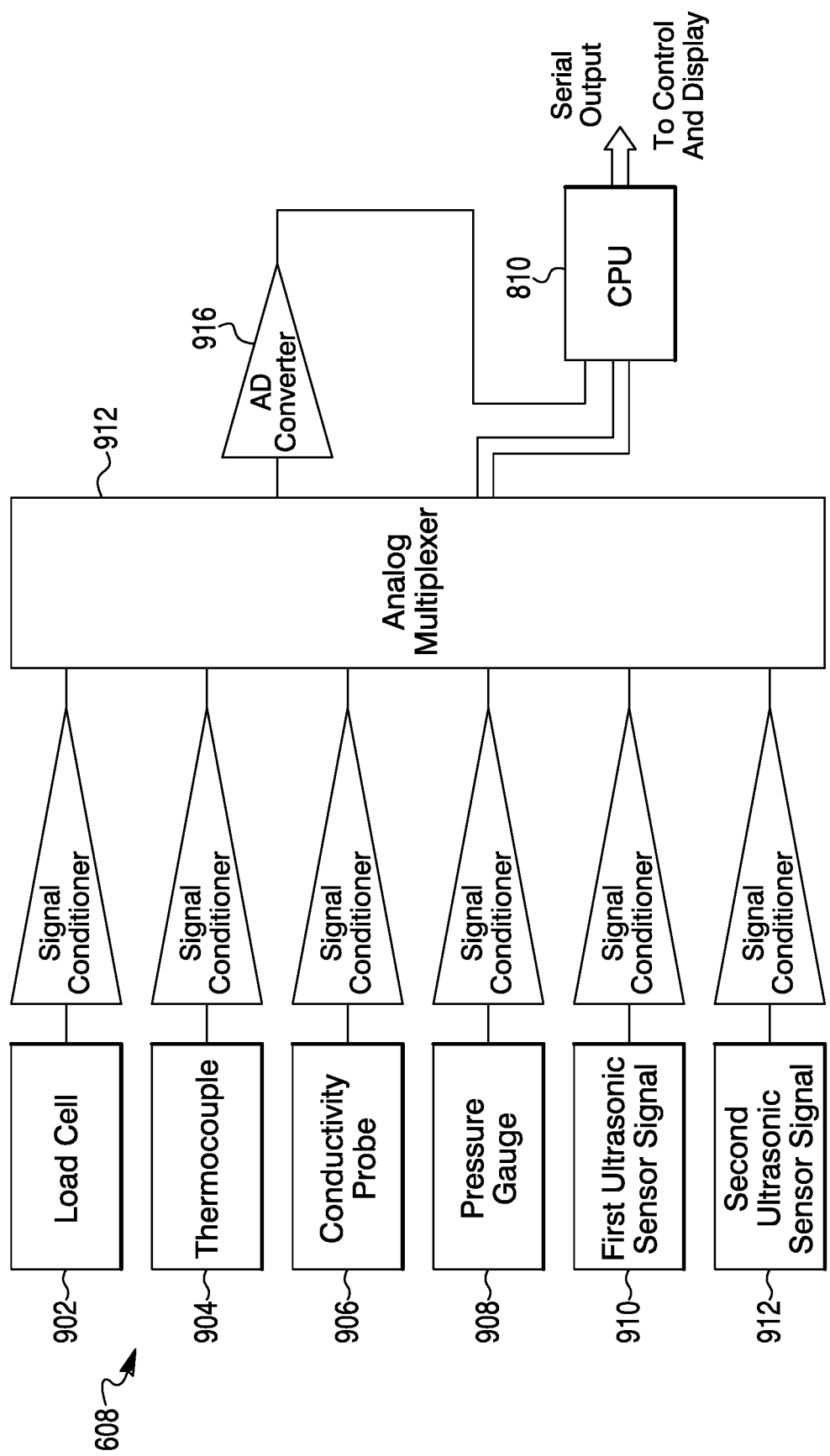
FIG. 9 is a schematic diagram of control circuitry for use with the borescope system of FIG. 8.
Figure 10:
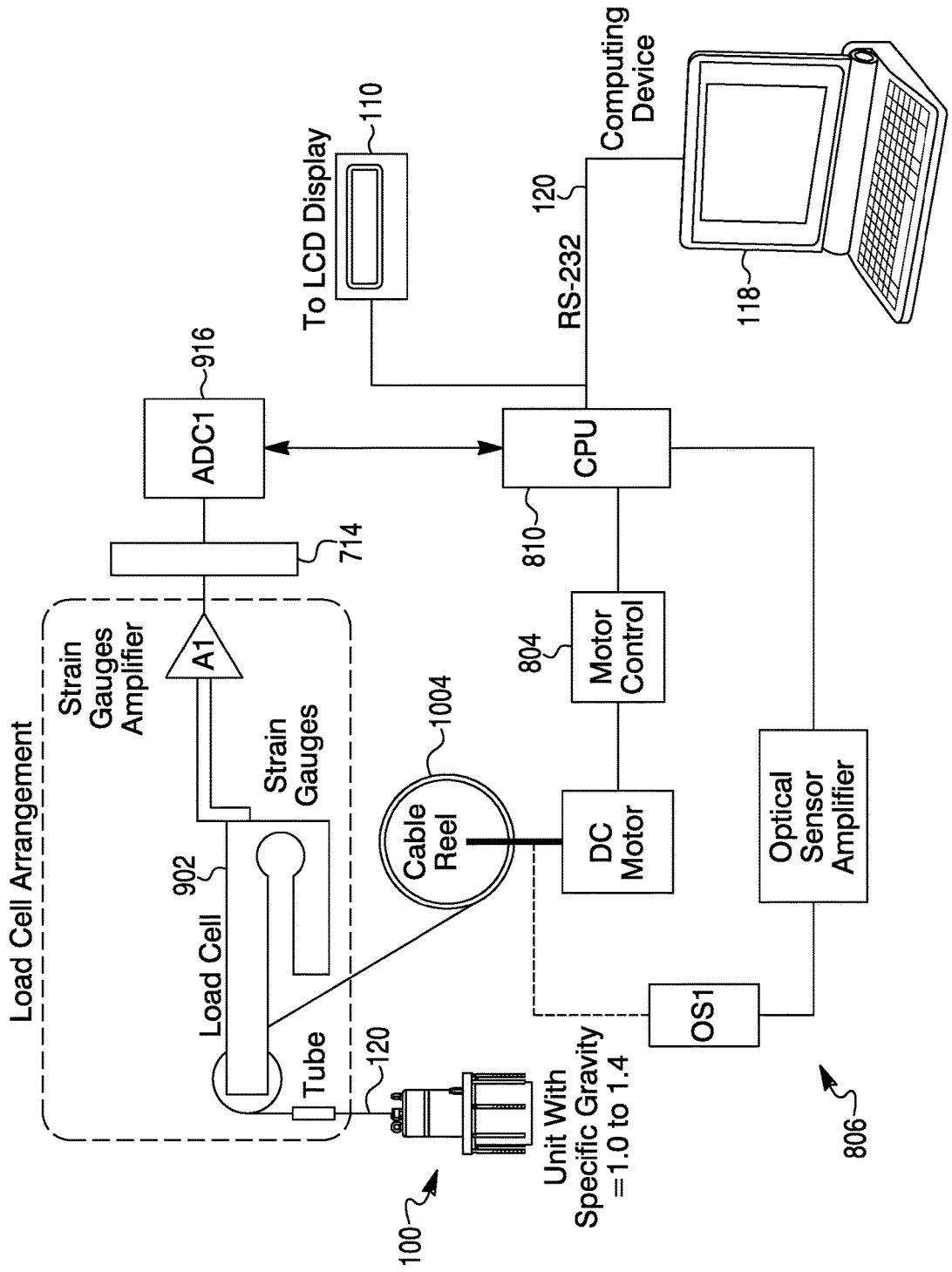
FIG. 10 is a schematic diagram of a load cell arrangement associated with the control circuitry of FIG. 9.

FIG. 10 shows an exemplary load cell arrangement including the load cell 902 of FIG. 9 for obtaining unit weight and viscosity measurements. Advantageously, the load cell arrangement permits determination of the unit weight and the viscosity of the slurry fluid, at different depths, as a function of the slurry's physical properties. For example, measurement assembly 100 including the fluid chamber (i.e., viewing envelope 510) has a predetermined specific gravity that ranges from 1 to 1.4. Based on the anticipated density of the slurry fluid in the borehole, the camera chamber size 212 can be selected to get the desired specific gravity (1 to 1.4). This specific gravity of the borescope is very important to determine the unit weight and the viscosity of the slurry fluid in the borehole.

The measurement assembly 100, can be lowered in the slurry fluid under a substantially constant velocity (i.e., a controlled fall). At different depth intervals, a control unit at the surface such as computer 118 detects its depth and buoyant weight from which the unit weight of the slurry can be determined. A digital readout unit at the surface displays the relationship between depths versus unit weight. In one embodiment, load cell 902, according to the arrangement of FIG. 10, determines the weight of measurement assembly 100 and the cable depth sensor 806 determines its depth. For example, cable depth sensor 806 comprises an optical wheel sensor 1002 associated with a cable reel 1004 used for raising and lowering measurement assembly 100 by its umbilical cord 120.

Moreover, the borescope system of the present disclosure provides qualitative as well as quantitative measurements to assist in determining the amount of sedimentary deposits and contamination in the boreholes rather than relying on the personal judgment of the drilled shaft inspector. When the disclosure is employed using a computer with MPEG or similar capability, the analog video images may be converted to digital images that an inspector or analyst can manipulate using digital filters, for example, to extract information that may not be detectable from a visual inspection of the shaft surfaces. For example, each pixel in an image would be mapped and given a value based on its optical characteristics. An image processor would then process the pixel data. In an alternative embodiment, a digital video camera may be used that provides both a video image as well as digital information regarding the image. Digital filtering and image processing techniques suitable for use with the present disclosure are known in the art and need not be described further herein. The digitized images and data can be added to a data base on drilled shaft construction and used to improve existing design/construction methods.

In one embodiment, the system comprises a portable inspection unit that can be transported and operated by a single inspector. Reconfiguring the basic unit to accommodate additional inspection sensors is also contemplated. Such sensors include probes to obtain soil specimens for further inspection, probes to measure penetration resistance of the bottom soil, or ultrasound or similar penetrating sensors to gather information below surficial sediments. These additions are regarded as accessories and may be added to the basic unit when field conditions require such accessories. Advantageously, such a system provides both portability and versatility to facilitate the process of shaft inspection in a timely manner. Thus, one or two inspectors can perform the job with great efficiency and without causing delays in the construction stage of the drilled shafts. Furthermore, the borescope system of the present disclosure is not limited to vertical drilled shafts and may be used to inspect non-vertical shafts by adjusting or substituting the structure used to support and/or suspend the camera and housing into the shaft.

Embodiments of the present disclosure may facilitate a borehole inspection process, and help avoid the need for deploying human inspectors into the boreholes. Measurements obtained by the present disclosure may help avoid parallax errors resulting from reading a scale at an angle.

The disclosure incorporates U.S. Pat. Nos. 7,187,784 and 8,169,477 in their entireties by references.

When introducing elements of the present disclosure or the embodiment(s) thereof, the articles "a," "an," "the," and "said" are intended to mean that there are one or more of the elements. The terms "comprising," "including," and "having" are intended to be inclusive and mean that there may be additional elements other than the listed elements.

In view of the above, it will be seen that the several objects of the disclosure are achieved and other advantageous results attained. As various changes could be made in the above constructions, products, and methods without departing from the scope of the disclosure, it is intended that all matter contained in the above description and shown in the accompanying drawings shall be interpreted as illustrative and not in a limiting sense.

We claim:

1. A borescope, comprising:
    a housing extending from a first end toward a second end, the housing including a first transparent viewing section extending circumferentially around a longitudinal axis of the housing and defining an exterior of a portion of the housing;
    a first imaging assembly configured to rotate about the longitudinal axis of the housing, and also pivot relative to the longitudinal axis of the housing;
    a second imaging assembly disposed within the housing, the second imaging assembly being configured to rotate about the longitudinal axis of the housing, wherein the second imaging assembly is configured to visualize a field of view exterior of the housing through the first transparent viewing section; and
    an expandable sleeve coupled to an exterior of the housing, wherein the expandable sleeve is configured to move from a collapsed position to an expanded position via application of a fluid through the sleeve.

2. The borescope of claim 1, further including a shaft extending at least partially through the housing, wherein the first imaging assembly and the second imaging assembly are both configured to rotate simultaneously about the longitudinal axis of the housing by rotation of the shaft.

3. The borescope of claim 1, further including a transparent observation chamber having a first end disposed at or adjacent to the second end of the housing, and extending away from both the first end and the second end of the housing, toward a second end.

4. The borescope of claim 3, wherein the second end of the observation chamber is configured to transition between a closed configuration where an exterior of the observation chamber forms a fluid-tight seal around a volume, and an open configuration where fluid can move into and out of the observation chamber through the second end.

5. The borescope of claim 1, further including a rigid support at a radially outermost portion of the expandable sleeve, the rigid support enclosing an opening through which the fluid can exit the expandable sleeve, wherein the second imaging assembly is configured to visualize a field of view exterior of the housing through the opening and the expandable sleeve.

6. The borescope of claim 5, wherein the expandable sleeve is coupled to the exterior of the housing by a transparent frame disposed circumferentially around the housing.

7. The borescope of claim 1, wherein, in the expanded position, the expandable sleeve extends only partially around a circumference of the housing.

8. A borescope, comprising:
    a housing extending from a first end toward a second end;
    a first imaging assembly configured to rotate about a longitudinal axis of the housing, and also pivot relative to the longitudinal axis of the housing;
    a transparent observation chamber having a first end disposed at or adjacent to the second end of the housing, and extending away from both the first end and the second end of the housing, toward a second end, wherein the transparent observation chamber is configured to transition between a closed configuration where an exterior of the observation chamber forms a fluid-tight seal around a volume, and an open configuration where fluid can move into and out of the observation chamber through the second end; and one or more rods at or adjacent to the second end of the housing, wherein:
each of the one or more rods extends from the second end of the housing and away from both the first end and the second end of the housing; and
each of the one or more rods includes a plurality of graduated markings forming a scale indicative of length, wherein each scale is visible to the first imaging assembly through the transparent observation chamber.

9. The borescope of claim 8, wherein the housing includes a first transparent viewing section extending circumferentially around the longitudinal axis of the housing and defining an exterior of a portion of the housing, and
the borescope further includes a second imaging assembly disposed within the housing, the second imaging assembly being configured to rotate about the longitudinal axis of the housing, wherein the second imaging assembly is configured to visualize a field of view exterior of the housing through the first transparent viewing section.

10. The borescope of claim 9, further including an expandable sleeve coupled to an exterior of the housing, wherein the expandable sleeve is configured to move from a collapsed position to an expanded position via application of a fluid through the sleeve.

11. A borescope, comprising:
a housing extending from a first end toward a second end, the housing including a first transparent viewing section extending circumferentially around a longitudinal axis of the housing and defining an exterior of a portion of the housing;
a first imaging assembly configured to rotate about a longitudinal axis of the housing, and also pivot relative to the longitudinal axis of the housing;
a second imaging assembly disposed within the housing, the second imaging assembly being configured to rotate about the longitudinal axis of the housing, wherein the second imaging assembly is configured to visualize a field of view exterior of the housing through the first transparent viewing section; and
an ultrasonic sensor at or adjacent to the second end of the housing, wherein the ultrasonic sensor is configured to determine a thickness of sediment disposed at a bottom of a borehole.

12. The borescope of claim 11, further including an expandable sleeve coupled to an exterior of the housing, wherein the expandable sleeve is configured to move from a collapsed position to an expanded position via application of a fluid through the sleeve.

13. A borescope, comprising:
a housing extending from a first end toward a second end;
a first imaging assembly configured to rotate about a longitudinal axis of the housing, and also pivot relative to the longitudinal axis of the housing;
a first ultrasound sensor configured to generate ultrasound waves; and
a reflector movable toward and away from the first ultrasound sensor along the longitudinal axis, or along a first axis parallel to the longitudinal axis, wherein the reflector is configured to reflect the ultrasound waves generated by the first ultrasound sensor back toward the first ultrasound sensor, and the first ultrasound sensor is configured to determine a time-of-flight for a wave to travel from the first ultrasound sensor to the reflector, and then back to the first ultrasound sensor wherein the housing includes a first transparent viewing section extending circumferentially around the longitudinal axis of the housing and defining an exterior of a portion of the housing, and the borescope further includes a second imaging assembly disposed within the housing, the second imaging assembly being configured to rotate about the longitudinal axis of the housing, wherein the second imaging assembly is configured to visualize a field of view exterior of the housing through the first transparent viewing section.

14. The borescope of claim 13, wherein:
the reflector is movable between a fully compressed position and a fully extended position;
the reflector is disposed closer to the first ultrasound sensor when in the fully compressed position than when in the fully extended position; and
the borescope further includes a biasing member configured to bias the reflector toward the fully extended position.

15. The borescope of claim 14, further including:
a rod having a first end and a second end, wherein the reflector is disposed at the first end of the rod; and
a tapered block disposed at the second end of the rod, wherein the tapered block tapers radially inward in a direction away from both the first end and the second end of the housing.

16. The borescope of claim 14, wherein the biasing member is a spring.

17. The borescope of claim 13, further including an expandable sleeve coupled to an exterior of the housing, wherein the expandable sleeve is configured to move from a collapsed position to an expanded position via application of a fluid through the sleeve.

18. A borescope, comprising:
a housing extending from a first end toward a second end, the housing including a first transparent viewing section extending circumferentially around a longitudinal axis of the housing and defining an exterior of a portion of the housing;
a first imaging assembly configured to rotate about a longitudinal axis of the housing, and also pivot relative to the longitudinal axis of the housing;
a second imaging assembly disposed within the housing, the second imaging assembly being configured to rotate about the longitudinal axis of the housing, wherein the second imaging assembly is configured to visualize a field of view exterior of the housing through the first transparent viewing section;
an ultrasound sensor configured to rotate about the longitudinal axis of the housing; and
a controller configured to receive measurements from the ultrasound sensor to determine a volume of a borehole in which the borescope is located.

19. The borescope of claim 18, further including a depth sensor configured to determine a depth of the borescope, wherein the controller is configured to receive measurements from the depth sensor, wherein determination of the volume of the borehole also is based on the measurements from the depth sensor.

* * * * *